US009429276B2

(12) United States Patent
Katsumoto

(10) Patent No.: US 9,429,276 B2
(45) Date of Patent: Aug. 30, 2016

(54) FLOW CHANNEL DEVICE, PARTICLE SORTING APPARATUS, PARTICLE OUTFLOW METHOD, AND PARTICLE SORTING METHOD

(71) Applicant: Sony Corporation, Tokyo (JP)

(72) Inventor: Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 61 days.

(21) Appl. No.: 14/184,904

(22) Filed: Feb. 20, 2014

(65) Prior Publication Data
US 2014/0261757 A1  Sep. 18, 2014

(30) Foreign Application Priority Data

Mar. 13, 2013  (JP) ................. 2013-049983

(51) Int. Cl.
| | |
|---|---|
| B07C 5/34 | (2006.01) |
| F17D 1/00 | (2006.01) |
| G01N 15/12 | (2006.01) |
| B07C 5/342 | (2006.01) |
| G01N 15/10 | (2006.01) |
| G01N 15/14 | (2006.01) |

(52) U.S. Cl.
CPC ............ *F17D 1/00* (2013.01); *G01N 15/1245* (2013.01); *G01N 15/1404* (2013.01); *B01L 2200/0652* (2013.01); *B01L 2300/0864* (2013.01); *B07C 5/342* (2013.01); *G01N 2015/1006* (2013.01); *G01N 2015/1236* (2013.01); *G01N 2015/1263* (2013.01); *G01N 2015/149* (2013.01); *G01N 2015/1413* (2013.01); *Y10T 137/4891* (2015.04)

(58) Field of Classification Search
CPC ........... B07C 5/34; B07C 5/342; B07C 5/36; B07C 5/362; G01N 15/1404; G01N 15/1459; G01N 15/1484; G01N 2015/1415; G01N 2015/149; G01N 2015/1409; B01L 2200/0652; B01L 2300/0819; B01L 2300/0864; B01L 2400/0403; B01L 2400/0475; B01L 2300/0867; B01L 2300/0877
USPC ........................ 209/210, 552, 644, 906, 932; 422/502–505, 507
See application file for complete search history.

(56) References Cited

U.S. PATENT DOCUMENTS

| | | | | |
|---|---|---|---|---|
| 3,710,933 A | * | 1/1973 | Fulwyler | ............. G01N 15/12 209/3.1 |
| 3,989,381 A | * | 11/1976 | Fulwyler | ............ G01N 15/1436 356/338 |
| 5,437,200 A | * | 8/1995 | Hollinger | ............ G01N 35/1097 73/863.73 |
| 5,985,216 A | * | 11/1999 | Rens | .................. G01N 15/1404 239/423 |

(Continued)

FOREIGN PATENT DOCUMENTS

| | | |
|---|---|---|
| JP | 2003-507739 A | 2/2003 |
| JP | 2012-098075 | 2/2012 |

*Primary Examiner* — Joseph C Rodriguez
(74) *Attorney, Agent, or Firm* — Chip Law Group

(57) ABSTRACT

A flow channel device includes an inflow unit into which a transfer fluid that transfers particles is caused to flow, a first outflow unit including an inflow port into which a part of the transfer fluid caused to flow from the inflow unit is caused to flow, a holding unit that is connected to the inflow port and holds particles, and a particle outflow port from which the particles held in the holding unit are caused to flow out to a predetermined flow channel area by the transfer fluid caused to flow from the inflow port, and a second outflow unit including a peripheral outflow channel through which another part of the transfer fluid caused to flow from the inflow unit is caused to flow out to a peripheral flow channel area that surrounds the predetermined flow channel area, the peripheral outflow channel surrounding at least the particle outflow port.

9 Claims, 24 Drawing Sheets

(56) References Cited

U.S. PATENT DOCUMENTS

| | | | | |
|---|---|---|---|---|
| 6,263,745 B1 * | 7/2001 | Buchanan | .......... | G01N 15/1404 73/865.5 |
| 7,355,696 B2 * | 4/2008 | Mueth | ................ | G01N 15/1404 209/3.1 |
| 7,392,908 B2 * | 7/2008 | Frazier | ............... | G01N 15/1459 209/3.1 |
| 7,544,326 B2 * | 6/2009 | Norton | ................... | G01N 15/14 356/335 |
| 7,746,466 B2 * | 6/2010 | Godin | ............... | B01L 3/502776 250/458.1 |
| 9,027,850 B2 * | 5/2015 | Buchanan | .......... | G01N 15/1404 239/102.1 |
| 2004/0260157 A1 * | 12/2004 | Montes | ................ | G01N 15/147 600/301 |
| 2008/0213821 A1 * | 9/2008 | Liu | ................... | B01L 3/502761 435/39 |
| 2012/0097582 A1 * | 4/2012 | Tsukii | ................ | G01N 15/1404 209/577 |

* cited by examiner

FLOW CHANNEL DEVICE, PARTICLE SORTING APPARATUS, PARTICLE OUTFLOW METHOD, AND PARTICLE SORTING METHOD

CROSS REFERENCE TO RELATED APPLICATIONS

This application claims the benefit of Japanese Priority Patent Application JP 2013-049983 filed Mar. 13, 2013, the entire contents of which are incorporated herein by reference.

BACKGROUND

The present technology relates to a flow channel device, a particle sorting apparatus, a particle outflow method, and a particle sorting method for circulating particles such as cells.

As apparatuses that sort particles such as cells, a fluorescence flow cytometer and a cell sorter are known. In those apparatuses, under an appropriate vibration condition (generally, an exit flow velocity of several m/s and a vibration count of tens of kHz), cells are closed in a gas-liquid interface at an ejection opening by a fluid, and charges are given to the cells at the same time. The cells fly as droplets in a direction in accordance with a charge quantity in air to which a static electric field is applied and are eventually sorted into a sorting container provided outside a flow channel.

The technology is useful in the case where the flow velocity is relatively high as described above. For a flow cytometer for a low flow velocity or a dielectric cytometer, it is difficult to make droplets and satisfy an ejection condition for the droplets. In view of this, it is desirable to perform a sorting operation in a flow channel having branches and hold cells on a rear stage.

As a sorting mechanism in the flow channel, a method for changing a flow direction of a fluid by using a piezoelectric element or the like and indirectly driving cells in the fluid has been proposed. However, the responsiveness of the mechanical element is an approximately millisecond. In consideration of the responsiveness of a pressure wave of the flow channel, a sorting speed for the cells has a limitation.

On the other hand, as a method for directly driving the cells, a dielectrophoresis method has been proposed. Japanese Patent Translation Publication No. 2003-507739 discloses that a difference of a dielectrophoretic force between cell types and a difference of a sedimentation rate therebetween are used, thereby separating cells by type which flow in a flow channel in which an electrode is provided. Further, Japanese Patent Application Laid-open No. 2012-98075 discloses a cell sorting method by which cells that flow in a flow channel are analyzed to determine whether the cells are targets to be sorted or not, and in accordance with a sorting signal transmitted on the basis of the determination result, an electric field is applied. By the method, it is possible to sort the cells as the sorting targets by a sufficient dielectrophoretic force.

SUMMARY

Concerning the sorting method for the cells disclosed in Japanese Patent Translation Publication No. 2003-507739, the difference of the dielectrophoretic force caused by the difference of particle types is significantly smaller as compared to the difference of the dielectrophoretic force caused by the difference of the size, the shape, or the like between particles. Therefore, it is expected that the sorting method disclosed in Japanese Patent Translation Publication No. 2003-507739 does not work well in the case where a particle group with a small difference which is practically demanded is used as a target. The sorting method disclosed in Japanese Patent Application Laid-open No. 2012-98075 is expected to fulfill the function well, but further improvement in accuracy is demanded.

In view of the above-mentioned circumstances, it is desirable to provide a flow channel device, a particle sorting apparatus, a particle outflow method, and a particle sorting method capable of sorting particles with high accuracy.

According to an embodiment of the present technology, there is provided a flow channel device including an inflow unit, a first outflow unit, and a second outflow unit.

Into the inflow unit, a transfer fluid that transfers particles is caused to flow.

The first outflow unit includes an inflow port into which a part of the transfer fluid caused to flow from the inflow unit is caused to flow, a holding unit that is connected to the inflow port and holds particles, and a particle outflow port from which the particles held in the holding unit are caused to flow out to a predetermined flow channel area by the transfer fluid caused to flow from the inflow port.

The second outflow unit includes a peripheral outflow channel through which another part of the transfer fluid caused to flow from the inflow unit is caused to flow out to a peripheral flow channel area that surrounds the predetermined flow channel area, the peripheral outflow channel surrounding at least the particle outflow port.

In the flow channel device, the part of the transfer fluid caused to flow from the inflow unit is caused to flow to the holding unit from the inflow port of the first outflow unit. Then, the particles in the holding unit are caused to flow out to the predetermined flow channel area from the particle outflow port. Around the particle outflow port, the peripheral outflow port of the second outflow unit is provided. Through the peripheral outflow channel, another part of the transfer fluid caused to flow from the inflow unit is caused to flow out to the peripheral flow channel area that surrounds the predetermined flow channel area. As a result, it is possible to cause the particles to stably flow out in the predetermined flow channel area. Consequently, it is also possible to sort the particles with high accuracy.

The first and second outflow units may respectively cause the particles and the transfer fluid to flow out as a laminar flow having a Reynolds number of 1 or less.

In the case where the particles and the transfer fluid are caused to flow as the laminar flow having the Reynolds number of 1 or less as described above, it is also possible to cause the particles to stably flow in the predetermined flow channel area.

The first and second outflow units may respectively cause the particles and the transfer fluid to flow out in such a manner that a ratio between a flow rate in the predetermined flow channel area and a flow rate in the peripheral flow channel area falls within a range of 1:2 to 1:100.

By causing the particles and the transfer fluid to flow out with the flow rate ratio that falls within the range as described above, it is possible to cause the particles to stably flow out.

The peripheral outflow channel may be disposed concentrically with the particle outflow port as a center.

As a result, it is possible to sufficiently surround the particles caused to flow out to the predetermined flow channel area by the transfer fluid caused to flow out to the peripheral flow channel area, with the result that the particles can be caused to stable flow out.

The holding unit may include a supply port for supplying the particles and a main body unit having a funnel-like shape. The supply port has a diameter larger than that of the particle outflow port, and the main body unit includes a tapered unit which connects the supply port and the particle outflow port with each other and a diameter of which is reduced from the supply port toward the particle outflow port.

By providing the main body unit having the funnel-like shape, it is possible to guide the particles to the particle outflow port smoothly and thus cause the particles to flow out to the predetermined flow channel area with high accuracy.

The supply port may be sealed by a sealing member.

In this way, the supply port may be sealed by the sealing member. By appropriately setting the structure or the like of the sealing member, it is also possible to adjust the pressure in the holding unit.

The supply port may be in a state of being released to an atmosphere.

In this way, the supply port may be in the state of being released to the atmosphere. As a result it is possible to simplify the structure of the holding unit.

The particle outflow port may have a diameter that is smaller than ten times a diameter of the particle.

With this structure, it is possible to cause the particles to flow out to the predetermined flow channel area with high accuracy.

According to another embodiment of the present disclosure, there is provided a particle sorting apparatus including the flow channel device, a flow channel, a plurality of branch units, and an electrical field application unit.

The flow channel is connected to the flow channel device, and in the flow channel, the particles and the transfer fluid caused to flow out from the flow channel device are caused to flow.

The plurality of branch channels are branched from the flow channel.

The electrical field application unit is capable of forming a guide electrical field in the flow channel in accordance with a sorting signal that gives an instruction to sort the particles. The guide electrical field guides the particles to a predetermined branch channel out of the plurality of branch channels.

According to another embodiment of the present disclosure, there is provided a particle outflow method including causing a transfer fluid that transfers particles to flow into an inflow unit.

A part of the transfer fluid caused to flow from the inflow unit is caused to flow into a holding unit that holds particles, thereby causing the particles held in the holding unit to flow out to a predetermined flow channel area through a particle outflow port.

Another part of the transfer fluid caused to flow from the inflow unit is caused to flow out to a peripheral flow channel area that surrounds the predetermined flow channel area via a peripheral outflow channel that surrounds the particle outflow port.

According to another embodiment of the present disclosure, there is provided a particle sorting method including causing a transfer fluid that transfers particles to flow into an inflow unit.

A part of the transfer fluid caused to flow from the inflow unit is caused to flow into a holding unit that holds particles, thereby causing the particles held in the holding unit to flow out to a predetermined flow channel area through a particle outflow port.

Another part of the transfer fluid caused to flow from the inflow unit is caused to flow out to a peripheral flow channel area that surrounds the predetermined flow channel area via a peripheral outflow channel that surrounds the particle outflow port.

The particles caused to flow out from the particle outflow port and the transfer fluid caused to flow out through the peripheral outflow channel are caused to flow to a flow channel; and A guide electrical field in the flow channel is formed in accordance with a sorting signal that gives an instruction to sort the particles by an electrical field application unit provided to the flow channel. The guide electrical field guides the particles to a predetermined branch channel out of a plurality of branch channels.

As described above, according to the embodiments of the present technology, it is possible to provide a flow channel device capable of sorting the particles with high accuracy.

These and other objects, features and advantages of the present technology will become more apparent in light of the following detailed description of best mode embodiments thereof, as illustrated in the accompanying drawings.

DETAILED DESCRIPTION OF EMBODIMENTS

Hereinafter, an embodiment of the present technology will be described with reference to the drawings.

(Structure of Particle Sorting Apparatus)

Figure 1:
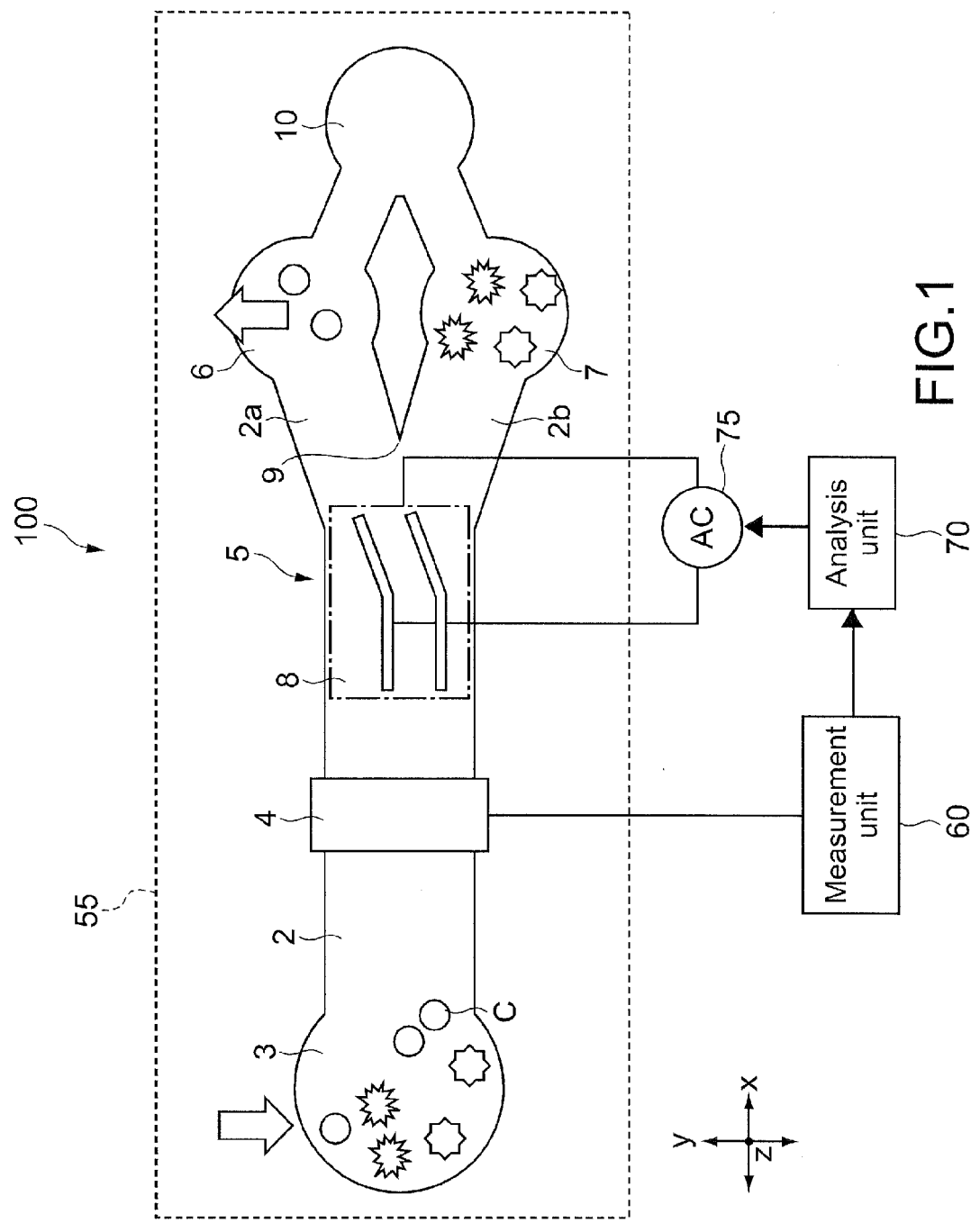
FIG. 1 is a schematic diagram showing the structure of a particle sorting apparatus according to an embodiment of the present technology.
Figure 2:
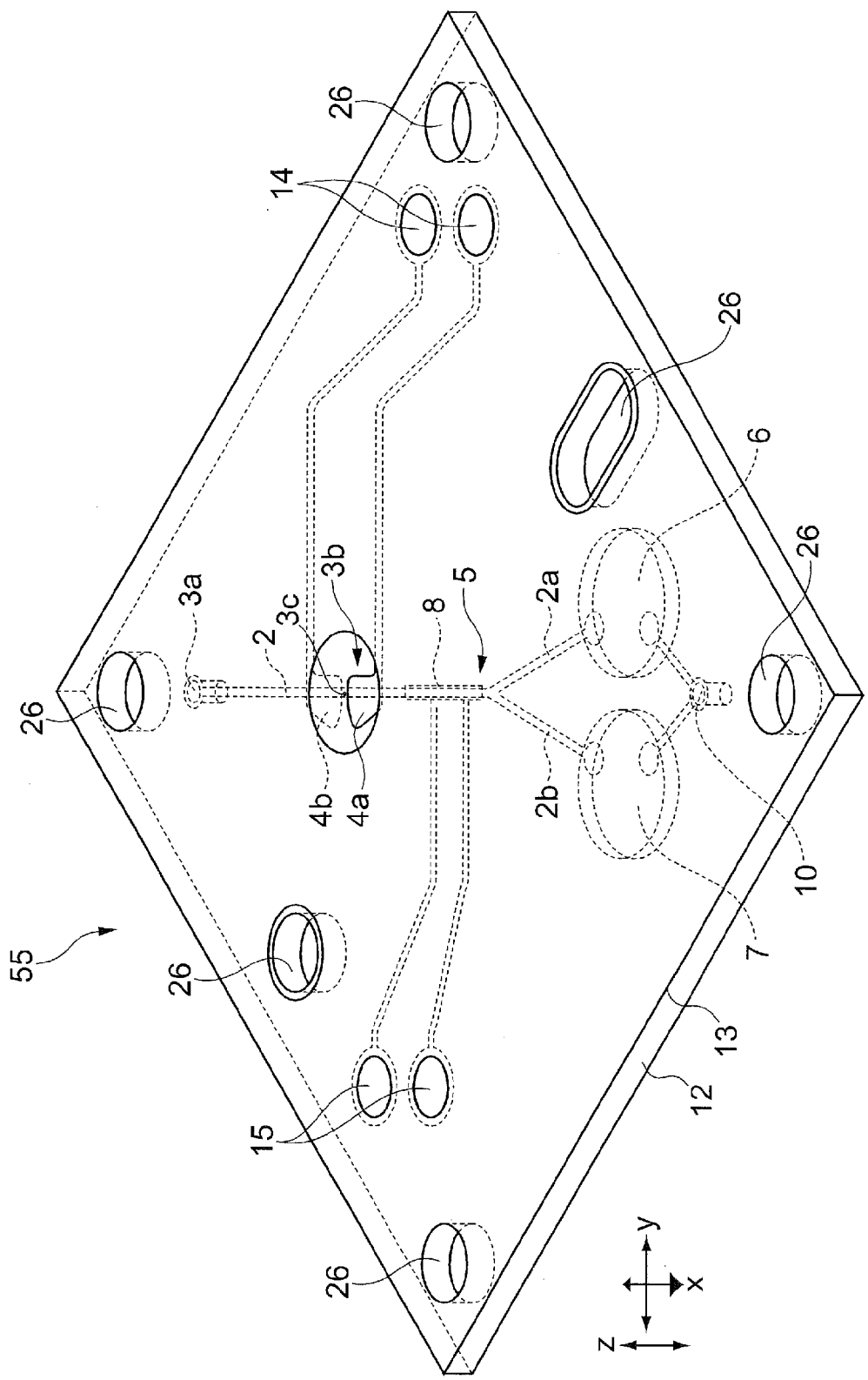
FIG. 2 is a perspective view showing an example of a sorting flow channel unit shown in FIG. 1.
Figure 3:
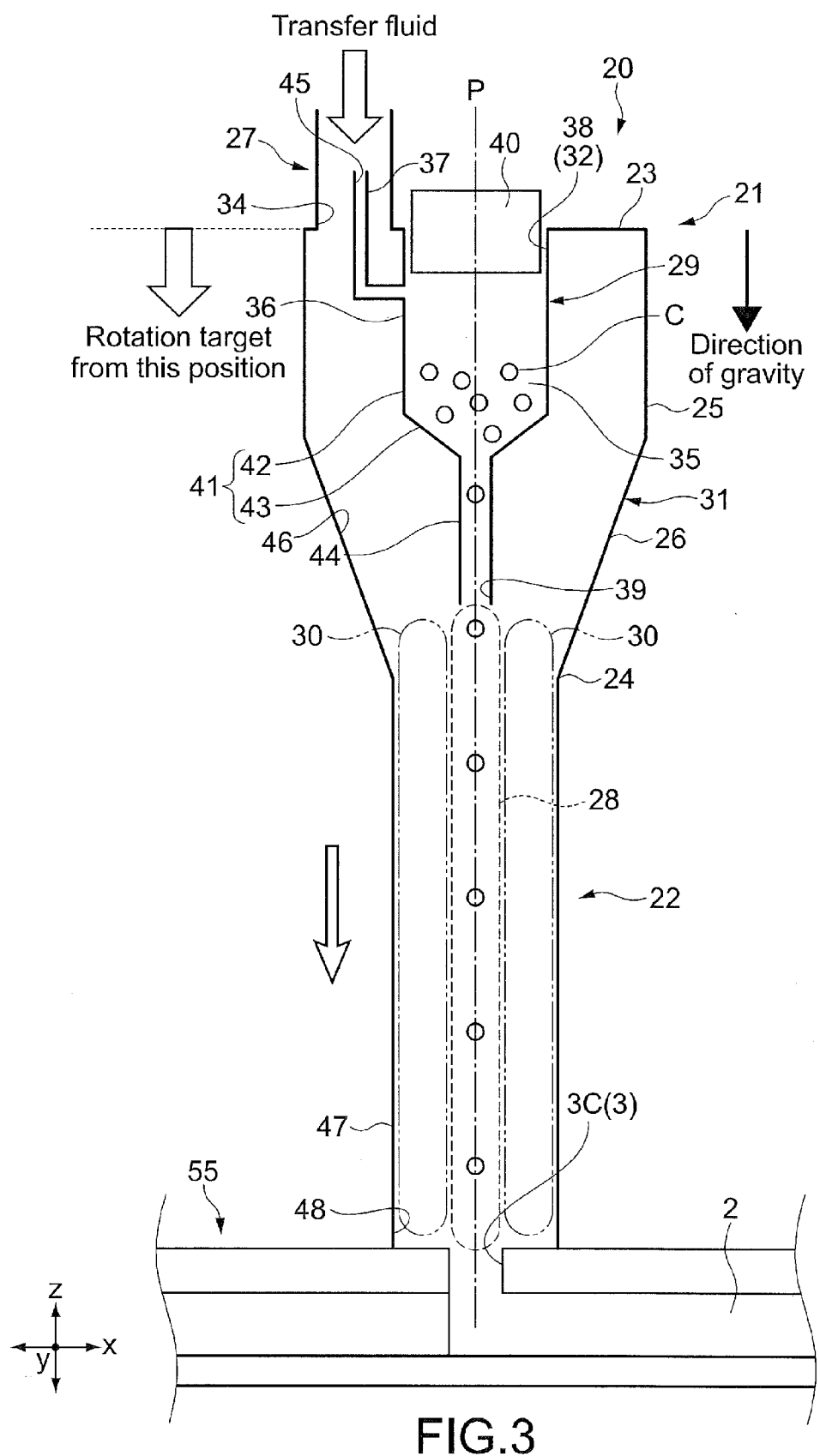
FIG. 3 is a schematic diagram showing the structure of a particle outflow unit according to this embodiment.

FIG. 1 is a schematic diagram showing the structure of a particle sorting apparatus according to an embodiment of the present technology. FIG. 2 is a perspective view showing an example of a sorting flow channel unit shown in FIG. 1. FIG. 3 is a schematic diagram showing the structure of a particle outflow unit as a flow channel device according to this embodiment.

As shown in FIG. 1, a particle sorting apparatus 100 is provided with a sorting flow channel unit 55, a measurement unit 60, and an analysis unit 70. In the sorting flow channel unit 55, from the upstream side thereof, an input unit 3, a flow channel (main flow channel) 2, a measurement electrode unit 4, a sorting unit 5, branch channels 2a and 2b, particle takeout units 6 and 7, and a discharge unit 10 are provided.

Into the input unit 3, a fluid (liquid) containing cells as particles C sampled is input through a particle outflow unit 20 shown in FIG. 3. In the flow channel 2, the liquid that is input from the input unit 3 flows. A direction of a main stream of the liquid is an x direction in FIG. 1.

In the measurement unit 60, an AC voltage having an arbitrary frequency within a predetermined frequency range is applied to the measurement electrode unit 4. For example, with respect to individual cells that flow in the flow channel 2, a complex dielectric constant that depends on each cell is measured for multipoint frequencies (three or more points, typically, about 10 to 20 points) within a frequency range (for example, 0.1 MHz to 50 MHz) of an AC voltage, in which a dielectric relaxation phenomenon occurs. It should be noted that the measurement unit 60 measures an impedance from a detection signal obtained from the measurement electrode unit 4 and obtains, from the impedance measured, the complex dielectric constant by a known electric conversion expression.

Examples of an amount electrically equivalent to the complex dielectric constant include a complex impedance, a complex admittance, a complex capacitance, a complex conductance, and the like. Those can be converted to each other by a simple electrical quantity conversion. Further, the measurement of the complex impedance or the complex dielectric constant includes a measurement of only a real part or only an imaginary part.

The analysis unit 70 receives information of the complex dielectric constant of the particles C measured by the measurement unit 60, determines whether the particles C have to be sorted or not on the basis of the complex dielectric constant, and in the case where the particles have to be sorted, generates a sorting signal. In this case, the analysis unit 70 functions as a signal generation unit.

Out of the plurality of kinds of particles C input from the input unit 3, the sorting unit 5 sorts particles C as targets into the particle takeout unit 6 and sorts remaining particles C into the particle takeout unit 7. The sorting unit 5 has a sorting electrode unit 8. A position on which the sorting electrode unit 8 is provided is a downstream side from a position on which the measurement electrode unit 4 is provided. The sorting unit 5 functions as an electrical field application unit in this embodiment.

The measurement unit 60 and the analysis unit 70 may be formed of hardware or formed of both of hardware and software. The measurement unit 60 and the analysis unit 70 may be one apparatus physically.

To the sorting electrode unit 8, a DC or AC drive voltage in accordance with the sorting signal output from the analysis unit 70 is applied. As a result, the sorting electrode unit 8 generates a guide electrical field in the flow channel 2. The guide electrical field is such an electrical field that the particles C are guided to predetermined one of the plurality of branches 2a and 2b.

The branches 2a and 2b are flow channels that are branched from the flow channel 2. The branch channel 2a is connected to the particle takeout unit 6, and the branch channel 2b is connected to the particle takeout unit 7. For example, in the case where the guide electrical field is not generated by the sorting electrode unit 8, the particles C flow to the particle takeout unit 7 through the branch channel 2b. On the other hand, in the case where the guide electrical field is generated in the flow channel 2 by the sorting electrode unit 8, the particles C flow to the particle takeout unit 6 through the branch channel 2a.

The particle takeout units 6 and 7 are communicated with the discharge unit 10. The liquid that has passed through the particle takeout units 6 and 7 is discharged to the outside from the discharge unit 10 by using a pump or the like.

Here, when the electrical field is applied to the particles C that exist in the liquid, an induced dipole moment is generated due to a difference of a polarizability between a medium (liquid) and the particles C. In the case where a space distribution of the applied electrical field, that is, a space distribution of an electrical flux density is not uniform, the electrical field intensity differs in the vicinity of the particles C, so a dielectrophoretic force expressed by the expression (1) is generated due to the induced dipole.

In the expression (1), $\in'm$, $\in v$, R, and Erms represent the real part of a complex relative permittivity (complex relative permittivity is defined by the expression (2)) of the medium, a vacuum dielectric constant, a particle radius, and an RMS (room mean square) value of the electrical field applied, respectively. Further, K is Clausius-Mossotti function expressed by the expression (3), and ∈*p and ∈*m represent dielectric constants of the particles C and the medium, respectively.

$$\langle \overline{F}_{DEP}(t) \rangle = 2\pi \varepsilon'_m \varepsilon_v R^3 \text{Re}[K(\omega)] \nabla E_{rms}^2 \quad (1)$$

$$\varepsilon^* = \varepsilon' - i\varepsilon'' + \frac{\kappa}{i\omega\varepsilon_v} \quad (2)$$

$$K(\omega) = \frac{\varepsilon^* p - \varepsilon^* m}{\varepsilon^* p + 2\varepsilon^* m} \quad (3)$$

As described above, in Japanese Patent Translation Publication No. 2003-507739, an attention is focused on a difference of K between particle types, and the particles are sorted by using only a dielectrophoresis method. In contrast, the particle sorting apparatus 100 according to the present technology does not use the difference of the dielectrophoretic force between particle types (frequency dependency). In accordance with the sorting signal transmitted from the analysis unit 70, the particle sorting apparatus 100 turns on and off the guide electrical field or performs an amplitude modulation and application, and performs sorting only for the particles C as the sorting targets by a sufficient dielectrophoretic force even if the particle groups have variations in particle size or physicality.

The particles C as the targets to be guided to the branch channel 2a by generating the guide electrical field by the sorting electrode unit 8 are referred to as target particles hereinafter. The particles C guided to the branch channel 2b without generating the guide electrical field are referred to as non-target particles hereinafter. The target particles and the non-target particles are normal cells and dead or cancerous cells, respectively, for example.

In advance, a storage device (not shown) only has to store information (and/or information of a range of the complex dielectric constant of the non-target particles) of a range of the complex dielectric constant of the target particles. The storage device is a device that is accessible by at least the analysis unit 70. On the basis of the information stored in the storage device, the analysis unit 70 determines whether the complex dielectric constant of the particles C which is measured by the measurement unit 60 falls within the range of the complex dielectric constant of the target particles or not (whether the complex dielectric constant of the particles C falls within the range of the complex dielectric constant of the non-target particles). The determination is performed in real time immediately after the measurement of the complex dielectric constant by the measurement unit 60. Then, in the case where the analysis unit 70 determines that the particles C as the measurement targets are target particles, the analysis unit 70 outputs the sorting signal and applies a predetermined drive voltage to the sorting electrode unit 8.

As shown in FIG. 2, in this embodiment, the sorting flow channel unit 55 has a chip shape and includes a substrate 12 and a sheet-shaped member 13 formed of a polymer film or the like. On the substrate 12, the flow channel 2, the branch channels 2a and 2b, a liquid input unit 3a serving as the input unit 3, the particle takeout units 6 and 7, and the discharge unit 10 are provided. Those are configured by forming grooves or the like on the surface of the substrate 12 and covering the surface with the sheet-shaped member 13.

A particle input unit 3b to which the liquid containing the particles C is input has a minute input hole 3c formed on the sheet-shaped member 13. Into the input hole 3c, the liquid containing the particles C is caused to flow by using the particle outflow unit 20 shown in FIG. 3. Then, the liquid caused to flow out is merged with the liquid that flows from the upstream side and flows to the downstream of the flow channel 2. By using the particle outflow unit 20 according to this embodiment, it is possible to cause the particles C to stably flow into the flow channel 2 with the particles C aligned.

A pair of measurement electrodes 4a and 4b is provided so that the input hole 3c is disposed therebetween. The measurement electrode 4a is provided on a front surface of the sheet-shaped member 13, and the measurement electrode 4b is provided on a back surface of the sheet-shaped member 13.

Upper portions of the particle takeout units 6 and 7 are covered with the sheet-shaped member 13. The sheet-shaped member 13 is stuck with a pipette, and the particles C are taken out via the pipette.

The measurement electrode unit 4 is electrically connected to electrode pads 14. The electrode pads 14 are connected to the measurement unit 60. The measurement unit 60 applies an AC voltage to the measurement electrode unit 4 through the electrode pads 14 and receives a detection signal from the measurement electrode unit 4 through the electrode pads 14.

The sorting electrode unit 8 in the sorting unit 5 is electrically connected to electrode pads 15. The analysis unit 70 applies a drive voltage to the sorting electrode unit 8 through the electrodes pads 15.

Through holes 26 are holes for fixation.

(Structure of Particle Outflow Unit (Flow Channel Device))

As shown in FIG. 3, the particle outflow unit 20 is disposed above the input hole 3c of the input unit 3 for a liquid. The particle outflow unit 20 causes the particles C to flow out to the input hole 3c in a direction of gravity. The particle outflow unit 20 is fixed to the sorting flow channel unit 55 by any fixation method. The sorting flow channel unit 55 and the particle outflow unit 20 may be integrally formed.

The particle outflow unit 20 includes an entire outflow unit 21 and an entire flow channel 22. The entire outflow unit 21 causes the particles C and a transfer fluid (also called as working fluid) that transfers the particles C to flow out. The entire flow channel 22 is connected to the entire outflow unit 21 and guides the particles C and the transfer fluid to the sorting flow channel unit 55. As shown in FIG. 3, the entire outflow unit 21 and the entire flow channel 22 are provided in such a manner that long axes thereof are along the direction of gravity. Further, the entire outflow unit 21 and the entire flow channel unit 22 each have an approximately columnar outside shape having a circular cross section taken along a plane in a direction (x-y plane direction) perpendicular to the long axis direction.

An upper surface 23 of the entire outflow unit 21 is a circular shape having the largest diameter. In contrast, a cross section of a connection part 24 between the entire outflow unit 21 and the entire flow channel 22, that is, a cross section of the entire flow channel 22 on the uppermost side is a circular shape, the diameter of which is smaller than the upper surface 23. A tapered unit 26 is formed in such a manner that a diameter thereof is gradually reduced from a part 25 in the middle of the entire outflow unit 21 in the z direction to the connection part 24. The shapes of the entire outflow unit 21 and the entire flow channel 22 are not limited and may be appropriately designed so as to be fit for the outflow of the particles C and the transfer fluid to be described later.

The entire outflow unit 21 includes an inflow unit 27 and a middle outflow unit 29 (first outflow unit). Into the inflow unit 27, the transfer fluid is caused to flow. The middle outflow unit 29 holds the particles C therein and causes the particles C to flow out to a middle flow channel area 28 (predetermined flow channel area) of the entire flow channel 22. The entire outflow unit 21 further includes a peripheral outflow unit (second outflow unit) 31 that causes the transfer fluid to flow out to a peripheral flow channel area 30 that surrounds the middle flow channel area 28.

Figure 4:
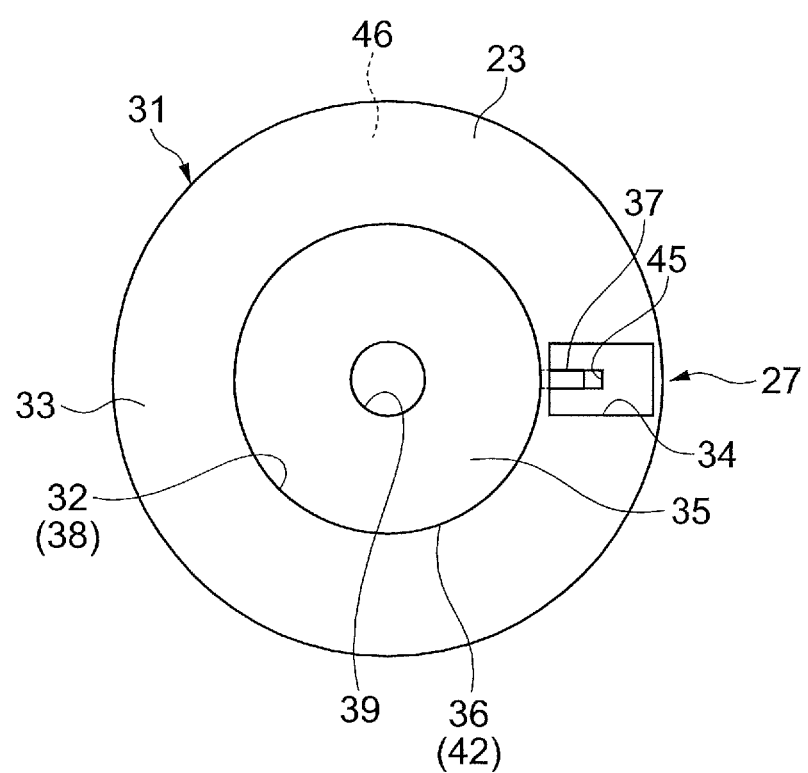
FIG. 4 is a schematic top view of an entire outflow unit shown in FIG. 3.

FIG. 4 is a schematic top view of the entire outflow unit 21. The upper surface 23 having the circular outer shape includes an opening 32 formed on the center thereof and an upper surface portion 33 that surrounds the opening 32. On a predetermined position of the upper surface portion 33, a transfer fluid inflow port 34 into which the transfer fluid is caused to flow is formed as the inflow unit 27. The other structure of the inflow unit 27 may be arbitrarily designed in such a manner that the transfer fluid can be appropriately caused to flow in the transfer fluid inflow port 34.

As shown in FIG. 3, the middle outflow unit 29 includes a main body 36 (holding unit) and a diverting route 37. The main body 36 has a space unit 35 therein. The diverting route 37 causes a part of the transfer fluid caused to flow from the transfer fluid inflow port 34 to send to the space unit 35 of the main body 36. The middle outflow unit 29 further includes a particle supply port 38 for supplying the particles C to the space unit 35 and a particle outflow port 39 for causing the particles C held in the space unit 35 to flow out to the middle flow channel area 28.

Above the main body 36, the particle supply port 38 is formed. In this embodiment, the opening 32 shown in FIG. 1 corresponds to the particle supply port 38. The particle supply port 38 is sealed by a sealing member 40 such as a movable stopper made of rubber or the like. Below the main body 36, the particle outflow port 39 is formed. The particle supply port 38 and the particle outflow port 39 are formed in such a manner that center axes P of the ports approximately coincide with each other in a direction in which the ports are opposed to each other in the z direction. Further, the particle supply port 38 is desired to have a larger diameter than the particle outflow port 39.

The shapes and the sizes of the particle supply port 38 and the particle outflow port 39 and the positional relationship therebetween are not limited to the above. The diameter of the particle outflow port 39 is designed in accordance with the diameter of the particle C caused to flow out, for example. For example, the particle outflow port 39 may be formed to have a diameter smaller than ten times the diameter of the particle C. In this case, it is possible to cause the particles C to flow out to the middle flow channel area 28 with high accuracy.

The main body 36 includes a main body unit 41 that connects the particle supply port 38 and the particle outflow port 39 with each other. The main body unit 41 includes a side wall unit 42 and a tapered unit 43 and has a funnel-like shape. The side wall unit 42 is extended downward so as to have a diameter which is approximately the same as the particle supply port 38. The tapered unit 43 has a diameter which is gradually reduced from the side wall unit 42 toward the particle outflow port 39. It should be noted that the shape of the main body 36 may be appropriately designed. By forming the funnel-shaped main body unit 41 as in this embodiment, it is possible to guide the particles C to the particle outflow port 39 smoothly. Further, as shown in FIG. 3, by disposing the particle outflow port 39 above the middle flow channel area 28 of the entire flow channel 22 relatively in the vicinity thereof, it is possible to cause the particles C to flow out to the middle flow channel area 28 with high accuracy.

In this embodiment, a part that is extended in the z direction so as to have a constant diameter from the lower end portion of the tapered unit 43 to the particle outflow port 39 is formed. Hereinafter, the part is referred to as a middle outflow channel 44. The particles C are caused to pass through the middle outflow channel 44 and flow out from the particle outflow port 39 to the middle flow channel area 28.

The diverting route 37 is connected to the side wall unit 42 of the main body 36. A tip of the diverting route 37 corresponds to an inflow port 45. The inflow port 45 and the main body 36 are communicated with each other via the diverting route 37. The inflow port 45 is opened upward so as to be opposed to the transfer fluid inflow port 34. Thus, when the transfer fluid is caused to flow in the transfer fluid inflow port 34, a part thereof is caused to flow in the inflow port 45 and is sent to the space unit 35 of the main body 36 via the diverting route 37. The shape and the size of the inflow port 45, the size of the diameter of the diverting route 37, and the like are not limited. For example, in order to set a flow channel resistance of the diverting route 37, a flow channel resistance from the inflow port 45 to the particle outflow port 39, or a flow rate ratio of the middle flow channel area 28 and the peripheral flow channel area 30 to be desirable, the diameter and the like of the diverting route 37 are designed appropriately.

The peripheral outflow unit 31 includes a peripheral outflow channel 46 that surrounds at least the particle outflow port 39. In this embodiment, the peripheral outflow channel 46 is formed so as to surround the entire main body 36. That is, an entire lower side part of the upper surface portion 33 shown in FIG. 1 forms the peripheral outflow channel 46. The peripheral outflow channel 46 is connected to the transfer fluid inflow port 34. Therefore, another part of the transfer fluid caused to flow from the transfer fluid inflow port 34, that is, the transfer fluid excluding the part that is caused to flow in the inflow port 45 of the main body 36 is caused to flow in the peripheral outflow channel 46 and then is caused to flow out to the peripheral flow channel area 30 of the entire flow channel 22 via the peripheral outflow channel 46.

The peripheral outflow channel 46 only has to surround at least the particle outflow port 39 and is not limited to such a structure as to entirely surround the main body 36 as in this embodiment. Further, typically, the peripheral outflow channel 46 is formed around the entire periphery of the particle outflow port 39. However, a plurality of peripheral outflow channels may be formed at intervals around the particle outflow port 39. In this case, around the particle outflow port 39, a plurality of outflow ports for causing the transfer fluid to flow out are formed.

The entire flow channel 22 includes a side wall unit 47 that is extended downward in the z direction, with the diameter of the connection part 24 with the entire outflow unit 21 maintained. The connection part 24 is a part where the particles C from the middle outflow unit 29 merge with the transfer fluid from the peripheral outflow channel 46. Hereinafter, the connection part may be referred to as a merged part 24. An area in the vicinity of a center axis P along a long-axis direction of the entire flow channel 22 corresponds to the middle flow channel area 28 to which the particles C are caused to flow out. An area in the vicinity of the side wall unit 47 which surrounds the center flow channel area 28 corresponds to the peripheral flow channel area 30. As shown in FIG. 3, on the outflow port 48 on the lower side of the entire flow channel 22, the particle outflow unit 20 is fixed to the sorting flow channel unit 55 in such a manner that the middle flow channel area 28 is disposed approximately on the center of the input hole 3c.

(Operation of Particle Outflow Unit (Flow Channel Device))

First, a sample containing the particles C is injected into the space unit 35 in the main body 36 with a pipette or the like with the movable stop removed. Typically, the sample containing the particles C is a liquid in which the particles C and the transfer fluid are mixed. That is, in the space unit 35 of the main body 36, the transfer fluid as the sample is injected in advance. The sample containing the particles C may be made of a material different from the transfer fluid. In this way, the main body 36 is used as a sample holder.

The way of injecting the sample into the main body 36 is not limited. As in this embodiment, in the case where the movable stop is removed, and the sample is injected with the pipette or the like, it is desirable that the pressure loss of the two flow channels (middle outflow channel 44 that is connected to the particle outflow port 39 and a narrow tube serving as the diverting route 37) that are connected with the space unit 35 is sufficiently increased. As a result, a flow caused by a pressure generated at the time of the injection with the pipette is directed upward, which is the atmosphere side, and thus leakage from the particle outflow port 39 or the like can be prevented. Upon completion of the injection of the sample to the main body 36, the particle supply port 38 is sealed with the movable stop.

Subsequently, the transfer fluid is caused to flow from the transfer fluid inflow port 34 formed on the upper surface portion 33. The transfer fluid caused to flow therein mostly passes through the peripheral outflow channel 46 and becomes an outer coaxial flow to be caused to flow out to the peripheral flow channel area 30 of the entire flow channel 22. On the other hand, the transfer fluid that is caused to flow in the inflow port 45 of the middle outflow unit 29 is caused to flow to the space unit 35 of the main body 36. By the pressure, the particles C held in the space unit 35 of the main body 36 are caused to flow out to the middle flow channel area 28 via the particle outflow port 39. At this time, the transfer fluid caused to flow in the main body 36 and the flow containing the particles C and the transfer fluid injected in advance become an inner coaxial flow and go out to the middle flow channel area 28. As a result, it is possible to cause the particles C to stably flow with the particles aligned in the middle flow channel area 28.

A ratio between the flow rate of the flow (hereinafter, referred to as middle flow) to the middle flow channel area 28 and the flow rate of the flow (hereinafter, referred to as peripheral flow) to the peripheral flow channel area 30 is determined as a reciprocal ratio of the flow channel resistances of the routes. Here, the diameter of the entire flow channel 22 is set as a typical length L, and an average flow velocity with respect to a cross section of the entire flow channel which is taken along an x-y plane direction is set as a typical velocity u. Further, a fluid kinematic viscosity of a mixture fluid (middle flow and peripheral flow) caused to flow through the entire flow channel 22 is represented by v. A Reynolds number Re is expressed by the following expression (4).

$$Re = Lu/v \quad (4)$$

In this embodiment, by the middle outflow unit 29 and the peripheral outflow unit 31, the particles C and the transfer fluid are caused to flow out as a laminar flow having the Reynolds number Re of 1 or less. In the case of the laminar flow area having a sufficiently small Reynolds number Re as described above, by sufficiently reducing the flow rate ratio of the middle flow to the peripheral flow, it is possible to stabilize the middle flow in the middle flow channel area 28 in the entire flow channel 22. Generally, if the diameter of the particle C is sufficiently small, inertia thereof is small. Thus, by the fluid viscosity, a velocity vector of the peripheral flow and a velocity vector of the particles C quickly become identical (small relief time). As a result, the particles C follow the middle flow and align and flow in the middle channel area 28. In this embodiment, the flow rate ratio between the middle flow and the peripheral flow is set to be approximately 1:9. Thus, it is possible to cause the particles C to stably flow in the middle flow channel area 28.

The numerical value of the flow rate ratio is not limited and may be set as necessary within such a range as to make an appropriate flow possible. For example, the particles C and the transfer fluid may be respectively caused to flow out in such a manner that the flow rate ratio between the middle flow and the peripheral flow falls within the range from 1:2 (1/2) to 1:100 (1/100). If the flow rate ratio between the middle flow and the peripheral flow is smaller than 1:2, that is, the peripheral flow is smaller than a double of the middle flow, the middle flow is increased immediately after being merged, and the particles C occupy approximately half of the flow channel width. This makes the control of the positions of the particles C difficult. If the flow rate ratio of the peripheral flow to the middle flow becomes larger, a property of going straight of the middle flow becomes better. However, if the flow ratio therebetween is larger than 1:100, that is, the peripheral flow becomes larger than 100 times the middle flow, the density of the particles C that occupy the entire flow is decreased, resulting in reduction of time efficiency for the measurement and sorting. In addition, the entire flow rate is excessively increased, and it is difficult to satisfy a passing velocity condition for the measurement unit or the like. It should be noted that in the case where the flow ratio is set to be larger than 1:100 with the entire flow rate fixed, the middle flow becomes significantly small. As a result, it may be impossible to perform stable liquid transmission.

In consideration of the points described above, the setting range of the flow rate ratio may be selected as appropriate within the range mentioned above. For example, the setting range of the flow rate ratio such as 1:10 to 1:70 and 1:30 to 1:50 may be selected as appropriate.

Figure 5:
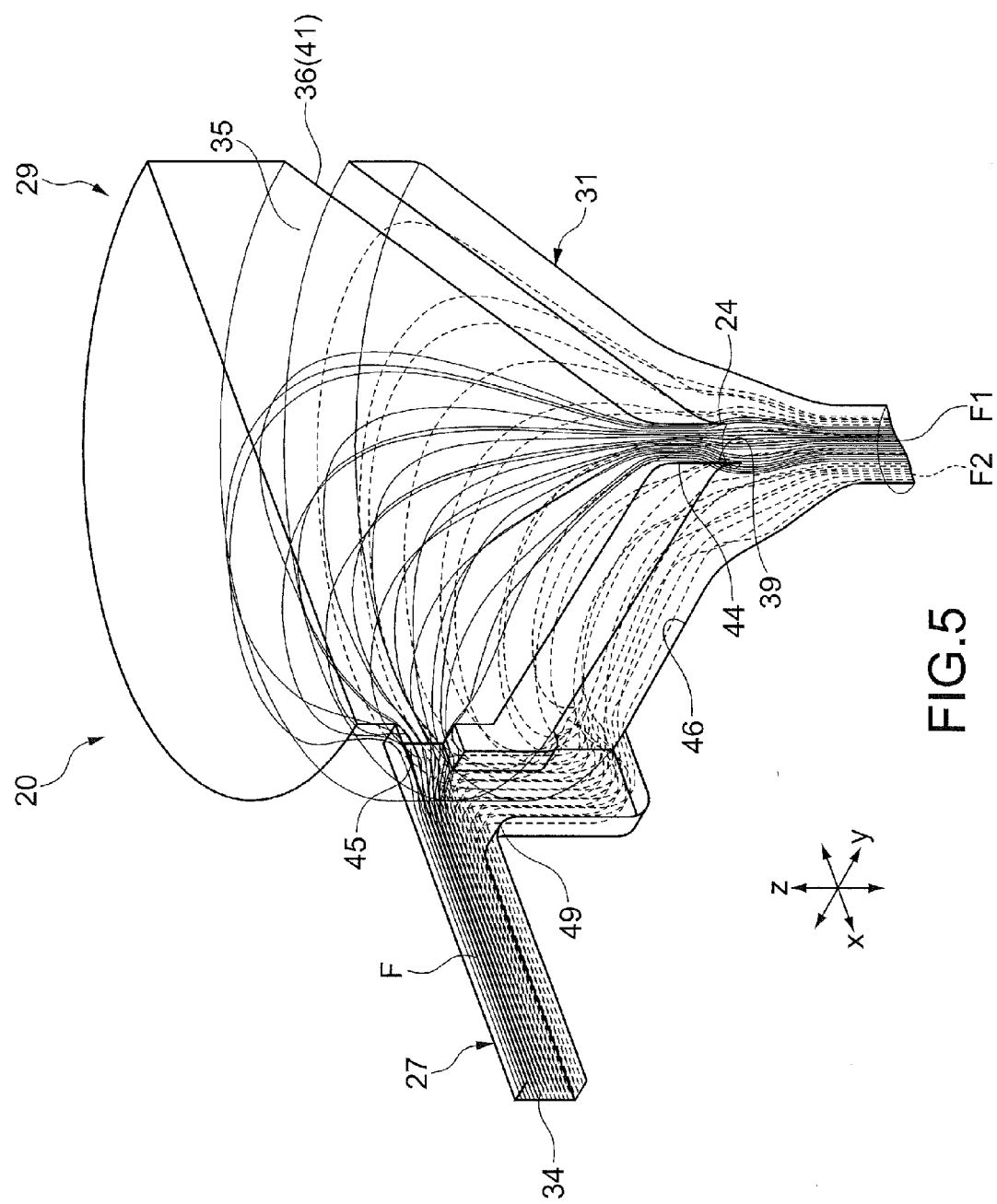
FIG. 5 is a diagram showing a more specific structural example of the particle outflow unit shown in FIG. 3.

FIG. 5 is a diagram showing a more specific structural example of the particle outflow unit 20 shown in FIG. 3. In FIG. 5, a structural example of a part corresponding to the entire outflow unit 21 shown in FIG. 1 is mainly described. Further, in FIG. 5, a flux of the middle flow caused to go out from the middle outflow channel 44 and a flux of the peripheral flow caused to go out from the peripheral outflow channel 46 are indicated on the basis of a numeric value calculation. The flux of the middle flow is indicated by solid lines, and the flux of the peripheral flow is indicated by broken lines. The applicant of the present disclosure can disclose the flow line graph of FIG. 5 (and flow line graph of FIG. 6) as color diagrams in which the fluxes are distinguished with colors.

In the particle outflow unit 20 shown in FIG. 5, a part protruded in the x direction (horizontal direction) on the left-hand side in the figure corresponds to the inflow unit 27 in which a transfer fluid F is caused to flow. On the tip of the inflow unit 27, the transfer fluid inflow port 34 is formed. From the port, the transfer fluid F is caused to flow therein. Advancing through the inside the inflow unit 27, the fluid reaches a branch unit 49. By the branch unit 49, the transfer fluid F caused to flow from the inflow unit 27 is split. A part of the transfer fluid F flows straight as it is and flows into the space unit 35 of the main body 36 via the inflow port 45 of the middle outflow unit 29. The transfer fluid F caused to flow in the space unit 35 is caused to flow along an inner surface of the main body unit 41 having a funnel-like shape. Then, the part of the transfer fluid F passes through the middle outflow channel 44 provided below the main body 36 and is caused to flow out as a middle flow F1 with particles (not shown) held in the space unit 35 from the particle outflow port 39.

By the branch unit 49 of the inflow unit 27, the other part of the transfer fluid F is split to the z direction. Then, the other part of the fluid is caused to flow into the peripheral outflow channel 46 of the peripheral outflow unit 31. Then, the transfer fluid F advances along an inner surface of the peripheral outflow channel 46 and is caused to flow out as a peripheral flow F2 that surrounds the middle flow F1.

In the structural example shown in FIG. 5, a flow resistance of the middle flow F1 relative to the peripheral flow F2 (flow channel resistance between the branch unit 49 and the merged part 24) is set to be ten times. As shown in the flow line graph, the middle flow F1 that is branched from the inflow unit 27 is surrounded by the peripheral flow F2 also branched from the inflow unit 27 and is caused to stably flow out to the downstream side.

Figure 6:
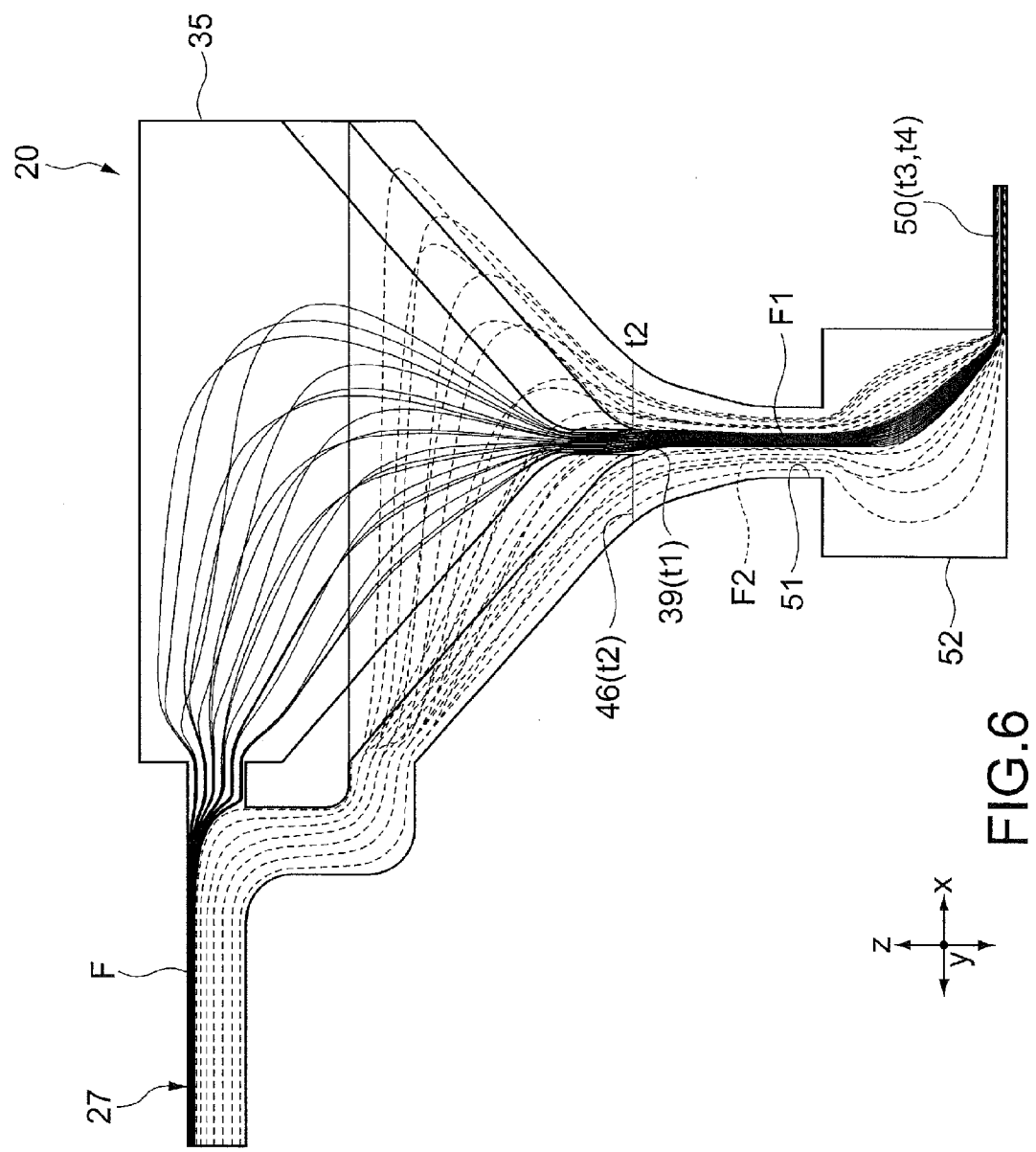
FIG. 6 is a diagram showing an example in which the particle outflow unit shown in FIG. 5 is expanded to a shape of an actual device with a main flow channel (micro flow channel) for causing the particles to flow, and a fluid numerical analysis is performed.

FIG. 6 is a diagram showing an example in which the particle outflow unit 20 shown in FIG. 5 is expanded to a shape of an actual device with a main flow channel (micro flow channel) 50 for causing the particles C to flow, and a fluid numerical analysis is performed. The main flow channel 50 shown in the figure is a flow channel having a rectangular cross section which is perpendicular to the middle flow F1 and corresponds to the flow channel 2 shown in FIG. 1. That is, FIG. 6 shows the analysis of how the middle flow F1 and the peripheral flow F2 that are caused to flow in the direction of gravity are transferred to the main flow channel 50 extended in the horizontal direction.

In this example, the flow channel resistance of the middle flow F1 is set to be 20 times as large as that of the peripheral flow F2. Further, a connection unit 52 is formed between the particle outflow unit 20 and the main flow channel 50. The connection unit 52 has a diameter larger than a diameter of an outflow port 51 from which the peripheral flow F2 is caused to flow out. On a position approximately the same as a bottom surface of the connection unit 52, the main flow channel 50 is formed so as to be extended from a side surface of the connection unit 52. As a result of the fluid numerical analysis with the structure as described above, it is found that the middle flow F1 is caused to flow into the main flow channel 50 having the rectangular cross section, with the middle flow F1 surrounded by the peripheral flow F2 while keeping a similar figure.

A description will be given on a result of experimental confirmation of the numerical analysis. In a particle outflow unit having the same structure as shown in FIG. 6, a diameter t1 of the particle outflow port 39 is set to 10 μm, and a diameter t2 of the peripheral outflow channel 46 is set to 100 μm. Then, a width t3 (size in the y direction) of the main flow channel 50 connected thereto is set to 250 μm, and a height t4 (size in the z direction) thereof is set to 50 μm. In the experiment, a sample obtained by suspending a great number of 10-μm polystyrene particles in water is injected to the main body 36. After that, the transfer fluid F is caused to flow from the inflow unit 27 by a volume flow rate of 1 μm per minute.

In the case where the particle outflow unit 20 provided with the flow adjustment structure according to the present technology, a standard deviation of the width of a particle distribution in a width direction in the main flow channel 50 was 4 μm. On the other hand, in the case where the sample containing the particle was caused to flow in the main flow channel 50 at the same flow rate without using the particle outflow unit 20, the particles flowed over approximately entire width direction. From this result, it is found that the particles can be caused to stably flow with the particles aligned by using the present technology.

As described above, in the particle outflow unit 20 as the flow channel device according to the present technology, the part of the transfer fluid F caused to flow from the transfer fluid inflow port 34 is caused to flow from the inflow port 45 of the middle outflow unit 29 into the main body 36. Then, the particles C in the main body 36 are caused to flow from the particle outflow port 39 to the middle flow channel area 28. Around the particle outflow port 39, the peripheral outflow channel 46 of the peripheral outflow unit 31 is disposed. Via the peripheral outflow channel 46, the other part of the transfer fluid F caused to flow from the transfer fluid inflow port 39 is caused to flow out to the peripheral flow channel area 30 that surrounds the middle flow channel area 28. As a result, it is possible to cause the particles C to stably flow out in the middle flow channel area 28. Consequently, it is possible to sort the particles with high accuracy in a sorting process of the particles (to be described later).

For example, it is thought that the middle flow F1 for causing the particles C to flow and the peripheral flow F2 for facilitating the flow adjustment of the particles are caused to flow in while being controlled independently of each other. That is, a flow called a sheath flow is caused to flow as the peripheral flow F2. However, in a minute flow rate area with approximately 1 μm per minute as in this embodiment, to configure an automatic control mechanism for maintaining the flow rate ratio between the middle flow F1 and the peripheral flow F2 to be constant or to measure the flow rate therefor is difficult, and thus precise control is difficult.

In this embodiment, the transfer fluid F caused to flow from the transfer fluid inflow port 34 is split and caused to flow into the middle outflow unit 29 and the peripheral outflow unit 31. As a result, as described above, the middle flow F1 and the peripheral flow F2 are caused to flow out with the constant flow rate ratio. That is, it is possible to maintain the flow rate ratio to be constant passively only by the transfer fluid F caused to flow from the transfer fluid inflow opening 34. Therefore, it is possible to stably align and cause the particles C to flow in the flow channel 50 without a specific flow rate automatic control method. By aligning the particles C, it is possible to improve analysis accuracy of an optical method, an electrical method, or the like for the particles C in the main flow channel 50 or on a later stage of the main flow channel 50. In addition, in the case where, by using some drive forces in the main flow channel 50 or on the later stage of the main flow channel 50, the particles C are sorted and extracted, it is possible to improve performance thereof.

Further, in the case where the particle outflow unit 20 according to the present technology is not used, it is difficult to exclude the possibility of mixture of a material derived from another sample, because the particles remain in a sample introduction tube in a sample introduction mechanism such as a particle analysis apparatus, or a particle suspension is brought into contact with the tube even once, for example. In contrast, in this embodiment, it is possible to cause the particles C to stably flow with the particles aligned and cause the sample suspension to stably flow in the middle flow channel area 28, with the result that the problem described above can be prevented.

Figure 7:
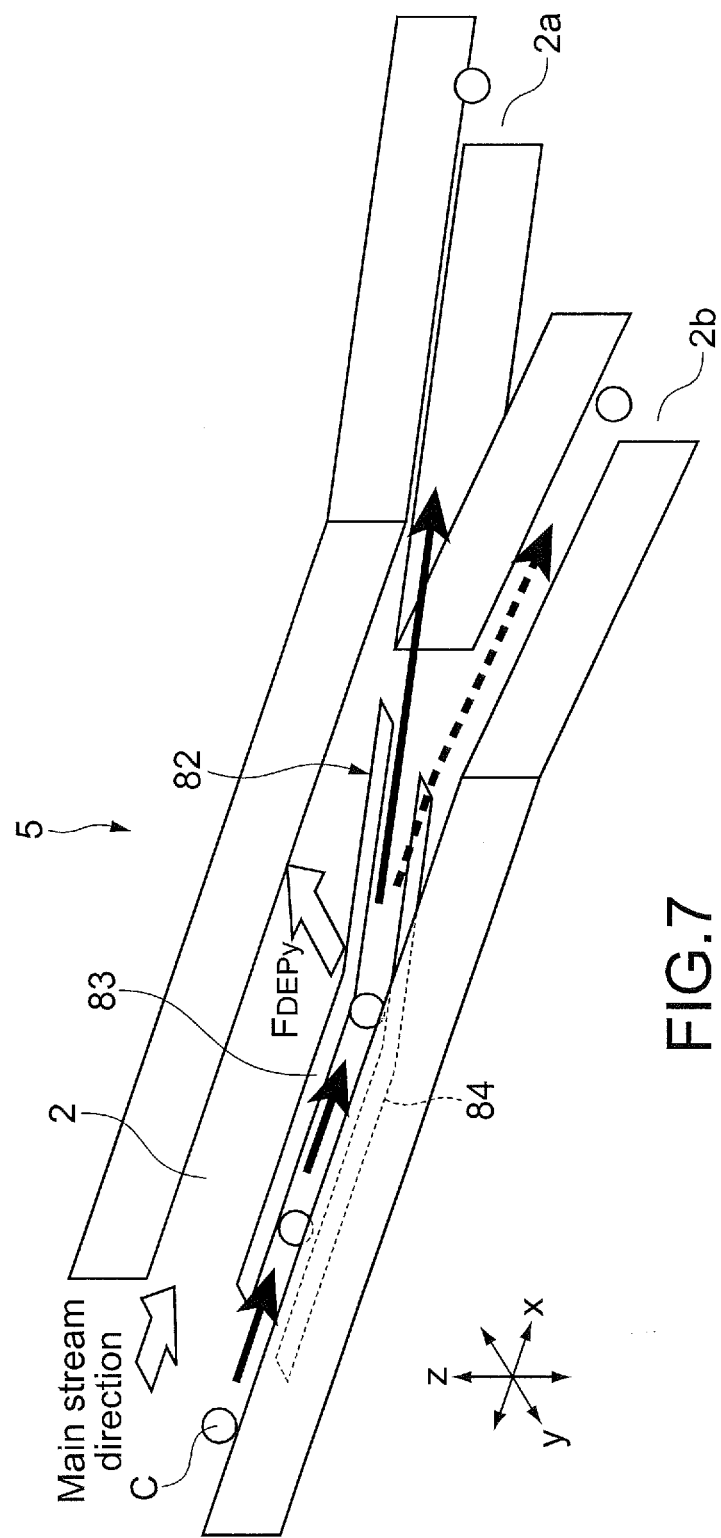
FIG. 7 is a perspective view showing a schematic structure of a sorting unit shown in FIG. 2.
Figure 8:
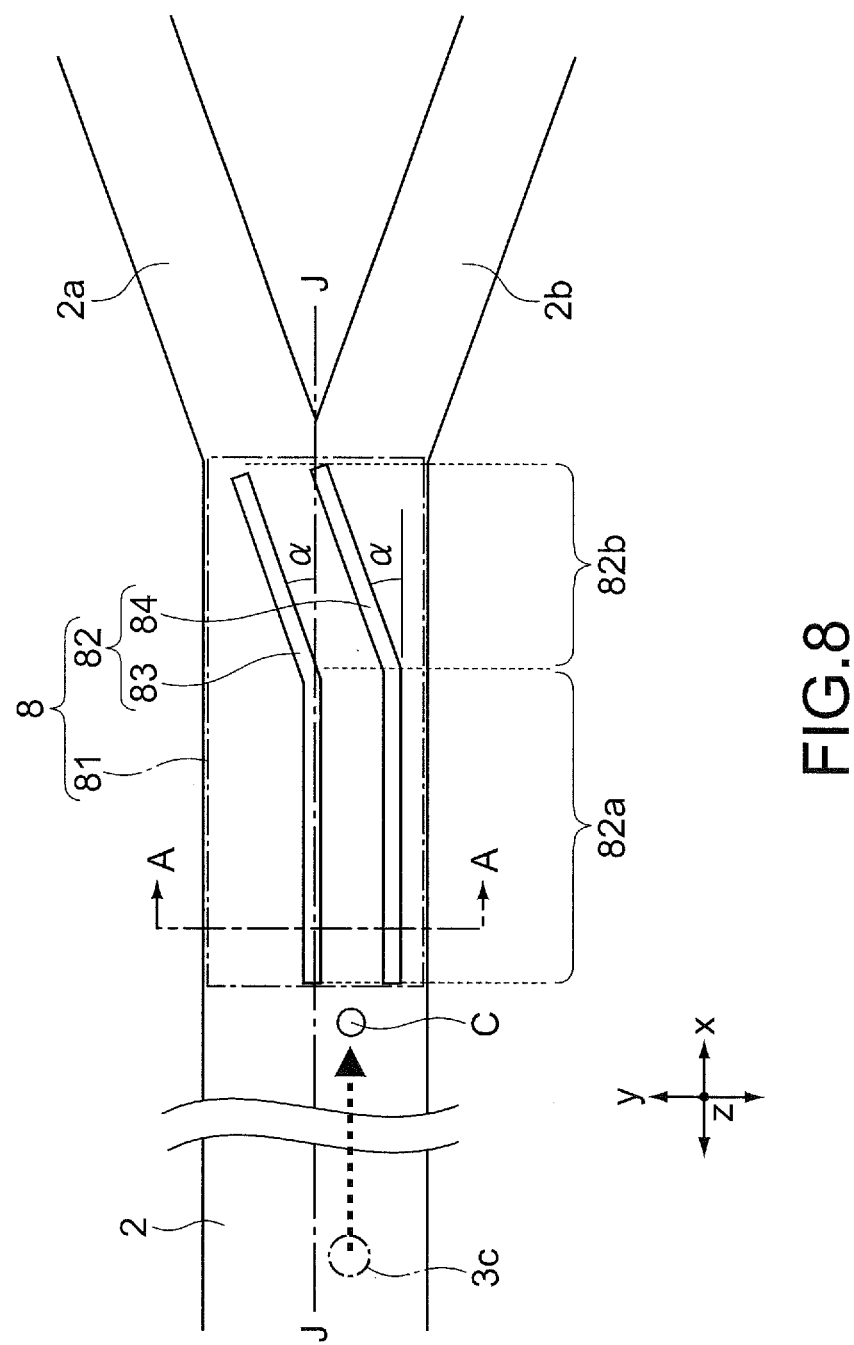
FIG. 8 is a plan view showing the sorting unit.
Figure 9:
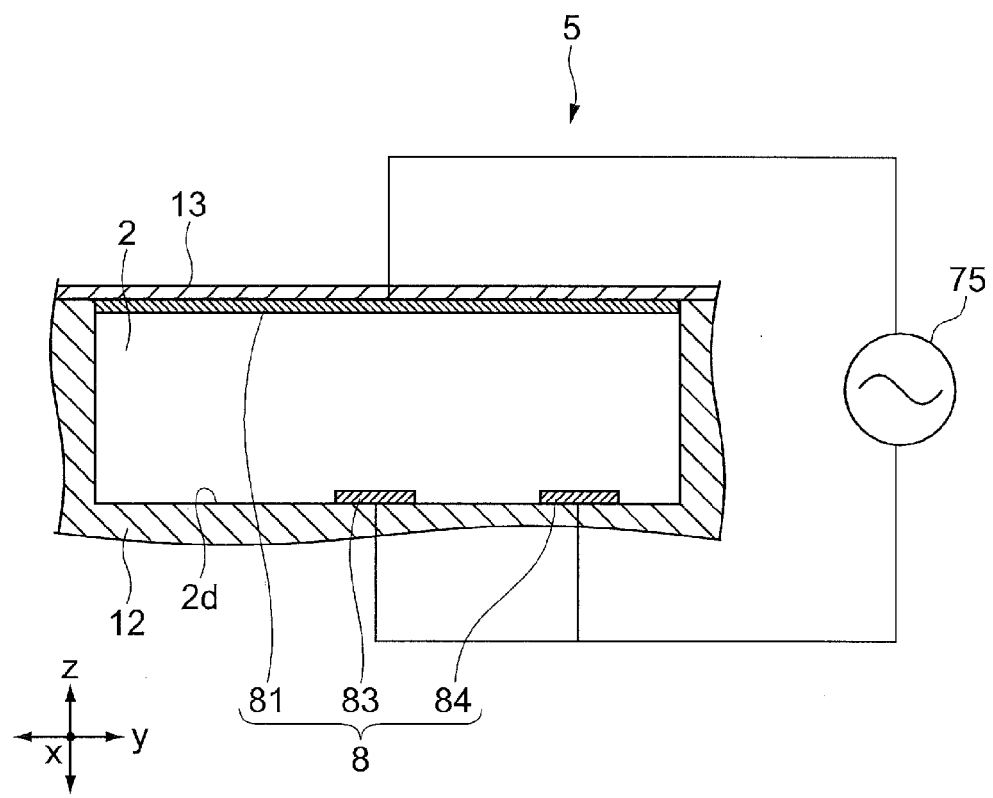
FIG. 9 is a cross-sectional diagram of the sorting unit shown in FIG. 8 which is taken along the line A-A.

FIG. 7 is a perspective view showing a schematic structure of the sorting unit 5 shown in FIG. 2. FIG. 8 is a plan view showing the sorting unit 5. FIG. 9 is a cross-sectional view of the sorting unit 5 taken along the linen A-A of FIG. 8.

The sorting electrode unit 8 is provided with a common electrode 81 having a first area and guide electrodes 83 and 84 each having a second area different from the first area. In this embodiment, the second area is smaller than the first area. In the following description, the pair of guide electrodes 83 and 84 is referred to as a "guide electrode structure 82".

The common electrode 81 is provided on the back surface side of the sheet-shaped member 13, for example, and the guide electrode structure 82 is provided on a bottom surface 2d in the flow channel 2. End portions of the common electrode 81 and the guide electrode structure 82 on the upstream side are disposed on the downstream side in relation to the particle input unit 3b, and end portions thereof on the downstream side are disposed on the upstream side in relation to the branch channels 2a and 2b.

The common electrode 81 may be provided on the front surface side of the sheet-shaped member 13, for example.

The common electrode 81 functions as a ground electrode. The common electrode 81 has a width in a y direction, which is substantially the same as the width of the flow channel 2 in the y direction, and has a length in the x direction to such an extent that the guide electrode structure 82 is covered therewith as shown in FIG. 8, for example. The common electrode 81 typically has a planar rectangular shape. The length of the common electrode 81 in the x direction may be longer or shorter than the length of the guide electrode structure 82 by a predetermined length.

The number of guide electrodes is multiple, for example, two. The guide electrodes 83 and 84 each have an elongated shape (band shape or rail shape) in a direction in which a liquid flows. One width of the guide electrode 83 or 84 in the y direction is formed to be smaller than that of the common electrode 81. The guide electrode structure 82 includes a linear portion 82a provided along the x direction, which is a mainstream direction of the liquid, and a direction change portion 82b provided so that a direction is changed from the linear portion 82a toward the branch channel 2a, that is, provided so as to be bent. A bend angle α (see, FIG. 8) will be described later. The linear portion 82a functions as an approach section of particles up to the direction change portion 82b.

As shown in FIG. 8, the linear portion 82a is disposed so as to be closer to the branch channel 2b side in the y direction in the flow channel 2. More specifically, in the linear portion 82a, an area between the guide electrode 83 on the inner side in the y direction in the flow channel 2 and the guide electrode 84 on the outer side is disposed on the branch channel 2b side in relation to a branch reference line J. The branch reference line J indicates a position of a branch point of the branch channels 2a and 2b in the y direction. The branch reference line J is substantially the center position in the flow channel 2 in the y direction.

To the common electrode 81 and the guide electrode structure 82, an AC power source 75 operated by the analysis unit 70 applies an AC voltage, for example. The common electrode 81 is connected to the ground as described above and is kept 0 V substantially. The two guide electrodes 83 and 84 each function as an active electrode that is driven at substantially the same potential. To those electrodes, a drive voltage having an amplitude of 1 to 30 V is applied. The frequency of the AC drive voltage is 1 kHz to 100 MHz.

As shown in FIG. 8, the input hole 3c provided in the particle input unit 3b is provided on the branch channel 2b side in the y direction in relation to the branch reference line J. With this structure, the particles C input from the input hole 3c can pass on the branch channel 2b side in the y direction in relation to the branch reference line J and can pass above the guide electrode structure 82.

(Sorting Operation by Sorting Flow Channel Unit)

Typically, intervals between particles C input through the particle input unit 3b are each set to at least a distance equal to or longer than a length of the sorting electrode unit 8 in the x direction. This is because the sorting unit 5 typically performs either one of an application of a guide electrical field for each particle C and a stop thereof, thereby performing sorting for each particle C. The flow velocity of the liquid (moving velocity of the particles C) can be set as appropriate, for example, set to approximately several mm/s. The velocity is capable of being controlled by a pump (not shown).

Figure 10:
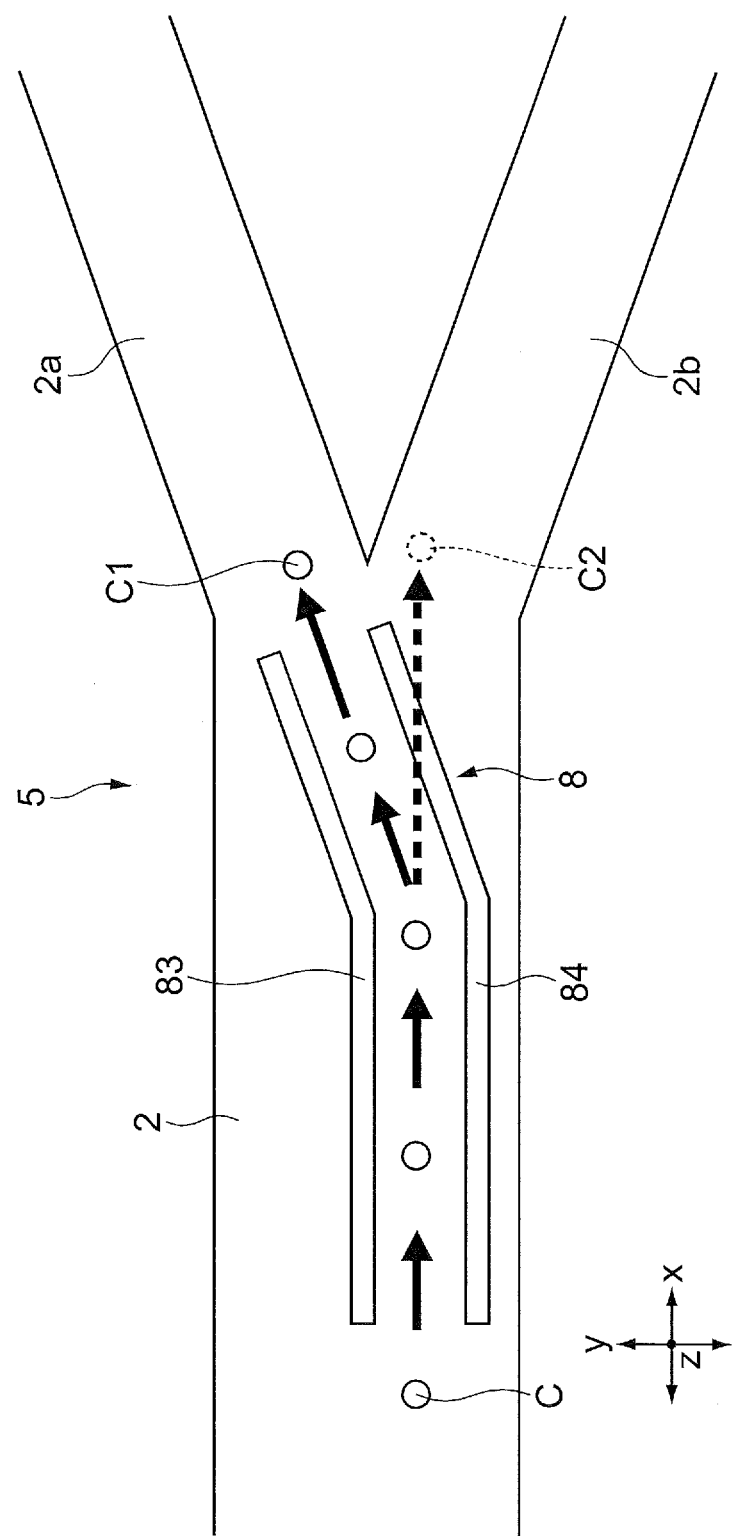
FIG. 10 is a diagram for explaining an operation of the sorting unit in a flow channel device.

In the case where the drive voltage is not applied to the sorting electrode unit 8, the guide electrical field is not formed. In this case, as shown in FIG. 10, non-target particles above the guide electrode structure 82 pass through the sorting electrode unit 8 while mostly maintaining the position in the y direction and flow into the branch channel 2b integrally with the flow of the liquid (see, particle C2).

In the case where the drive voltage is applied to the sorting electrode unit 8, a dielectrophoretic force toward the y direction is given to the target particles above the guide electrode structure 82 by the guide electrical field. As will be described later, the guide electrical field gives the target particles such a dielectrophoretic force that the target particles are disposed between the two guide electrodes 83 and 84. Thus, the target particles move along with the liquid so as to be disposed between the guide electrodes 83 and 84. As a result, a target particle C1 flows into the branch channel 2a.

The drive voltage is applied to the guide electrode 83 at timing before the target particle flows into the sorting electrode unit 8. The timing of the application of the drive voltage is preset in accordance with a distance from the input hole 3c to the sorting electrode unit 8, the flow velocity of the liquid, and the like.

In this embodiment, by the particle outflow unit 20 having the flow adjustment structure, the particles C are input to the input hole 3c with the particles aligned. Therefore, it is possible to cause the particles C to stably flow on the appropriate position in the flow channel 2. As a result, by applying the guide electrical field, the dielectrophoretic force of the target particle C1 can be appropriately generated. Consequently, it is possible to sort the particles C with high accuracy.

(Dielectrophoretic Force by Guide Electrical Field)

A. Generation Principle

The dielectrophoretic force has a property of being formed in a direction from an area having a stronger electrical field to an area having a weaker electrical field. The more abrupt difference in the intensity of the electrical field is caused, the larger the dielectrophoretic force becomes. In the present technology, an area having a weaker electrical field is formed between the guide electrodes 83 and 84. As a result, in an area from, for example, an edge of the guide electrode 83 (or 84) to the center between the guide electrodes 83 and 84, an abrupt difference in the intensity of the electrical field is generated. The guide electrical field is in such a state, thereby positioning the target particle C1 in the area in the guide electrode 83.

B. Example of Sorting Electrode Unit

Figure 11:
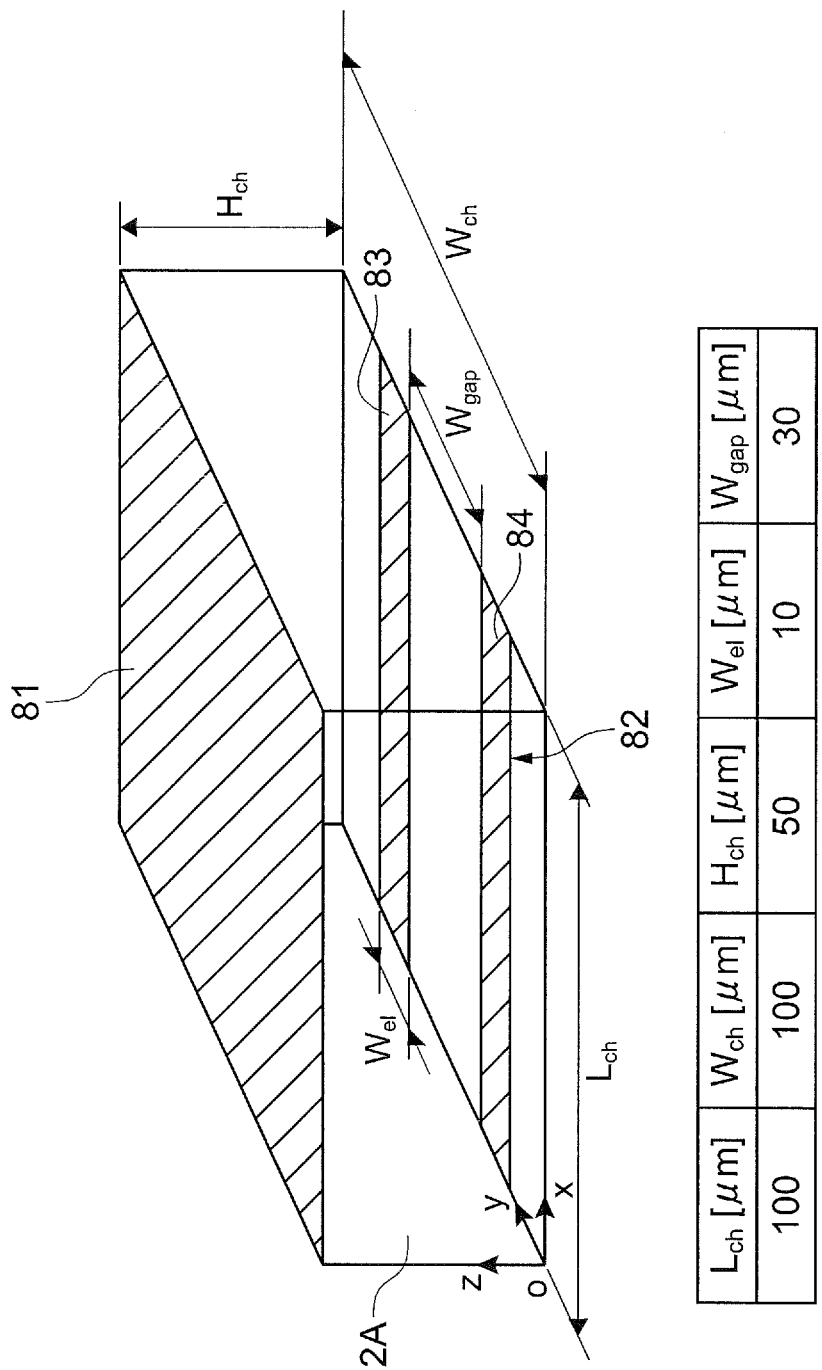
FIG. 11 is an example showing sizes of parts of a sorting electrode unit.

FIG. 11 is a diagram showing an example of sizes of parts of the sorting electrode unit. FIGS. 12 to 14 are diagrams each showing a simulation result of an electrical field intensity distribution for explaining the guide electrical field generated by the sorting electrode unit shown in FIG. 11. In those figures, to make it easy to grasp the electrical field intensity distribution, auxiliary lines are drawn with broken lines. In actuality, the applicant of the present technology can disclose FIGS. 12 to 14 as color figures.

As shown in FIG. 11, a flow channel 2A having a rectangular parallelepiped shape is provided. As the sizes of the flow channel 2A, a length in the mainstream direction (x direction), a width, and a height are set to Lch (=100 μm), Wch (=100 μm), and Hch (=50 μm), respectively. A length of the common electrode 81 in the mainstream direction and a width thereof are set to Lch and Wch, respectively. A length of each guide electrode in the mainstream direction and a width thereof are set to Lch and Wel (=10 μm), respectively. Further, a width of an area of a gap in the guide electrode structure 82 is set to Wgap (=30 μm). The unit of an electrical field E in this case is kV/m.

Figure 12A:
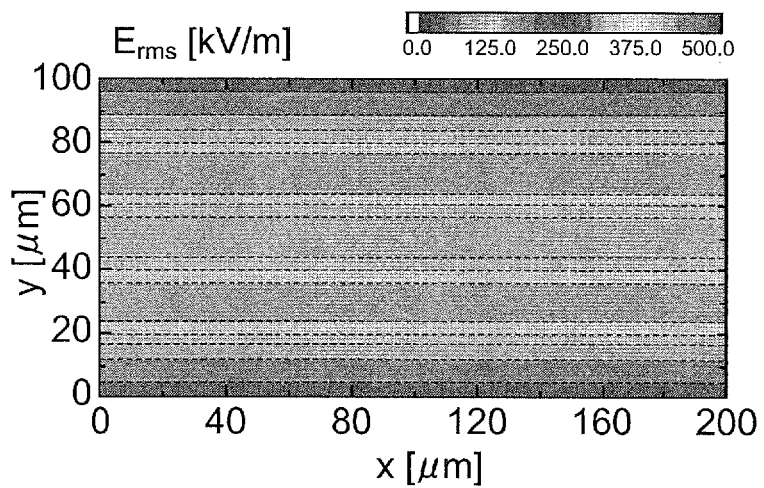
FIG. 12A is a diagram showing an electrical field intensity distribution on an x-y plane at the position of z=10 μm.
Figure 12B:
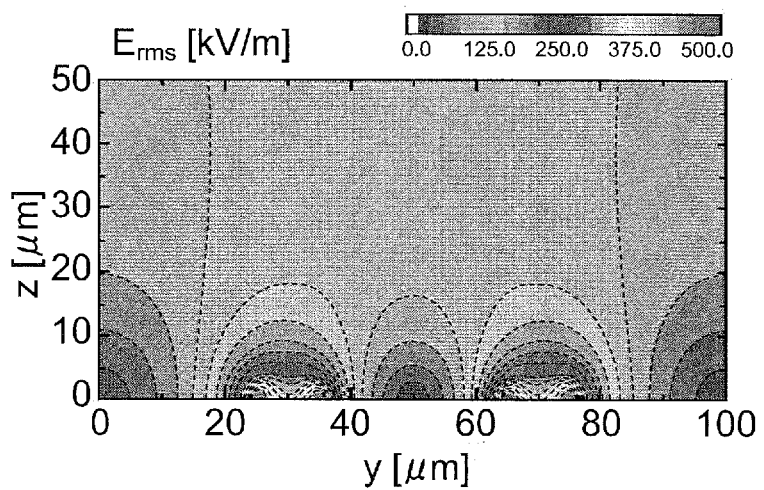
FIG. 12B is a diagram showing an electrical field intensity distribution on a y-z plane at the position of x=50 μm.

FIG. 12A shows an electrical field intensity distribution on an x-y plane at a position of z=10 μm in the height direction. FIG. 12B shows an electrical field intensity distribution on a y-z plane at a position of x=50 μm in the mainstream direction. The guide electrodes (83 and 84) are disposed within ranges of 25 to 35 μm and 65 to 75 μm, respectively, in the range of 0 to 100 μm in the y direction.

Figure 13A:
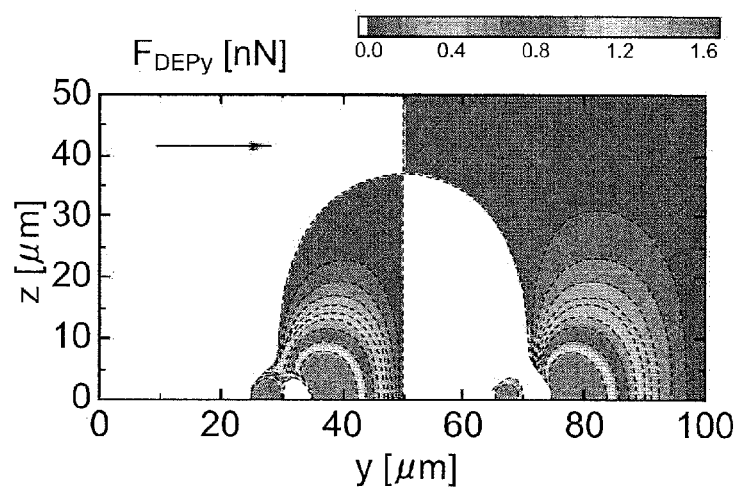
FIG. 13A is a diagram showing an intensity distribution of a dielectrophoretic force generated in a rightward y direction on a y-z plane at a position of x=50 μm.
Figure 13B:
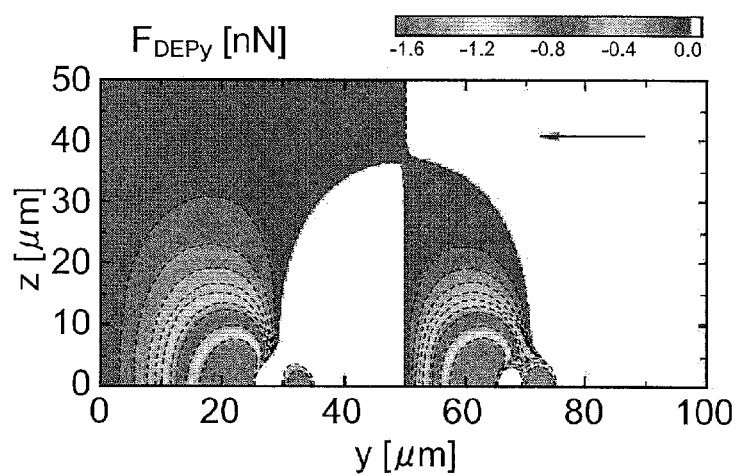
FIG. 13B is a diagram showing an intensity distribution of a dielectrophoretic force generated in a leftward y direction thereon.
Figure 14A:
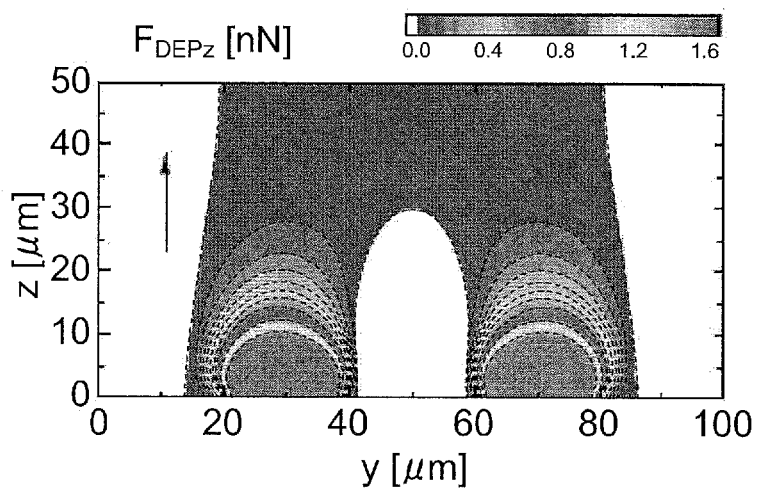
FIG. 14A is a diagram showing an intensity distribution of a dielectrophoretic force generated in an upward z direction on a y-z plane at a position of x=50 μm.
Figure 14B:
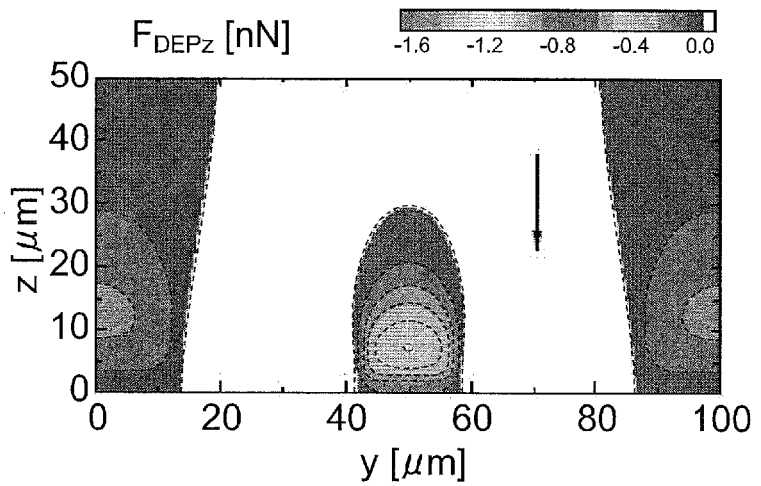
FIG. 14B is a diagram showing an intensity distribution of a dielectrophoretic force generated in a downward z direction thereon.

FIG. 13A shows an intensity distribution of a dielectrophoretic force generated only rightward in the figure, out of a dielectrophoretic force $F_{DEPy}$ that operates in the y direction on the y-z plane at the position of x=50 μm. Similarly, FIG. 13B shows an intensity distribution of a dielectrophoretic force generated only leftward in the figure, out of the dielectrophoretic force $F_{DEPy}$ on the y-z plane at the position of x=50 μm. FIG. 14A shows an intensity distribution of a dielectrophoretic force generated only upward in the figure, out of a dielectrophoretic force $F_{DEPz}$ that operates in the z direction on the y-z plane at the position of x=50 μm. FIG. 14B shows an intensity distribution of a dielectrophoretic force generated only downward in the figure, out of the dielectrophoretic force $F_{DEPz}$ on the y-z plane at the position of x=50 μm.

FIGS. 13A and 13B show the distributions having forms obtained by inverting each other, and the same holds true for FIGS. 14A and 14B. For example, the white area of FIG. 13A shows that the dielectrophoretic force that operates leftward is distributed, and the white area of FIG. 13B shows that the dielectrophoretic force that operates rightward is distributed. The same holds true for FIGS. 14A and 14B.

The dielectrophoretic force can be calculated on the basis of the above expression (1). The unit of the dielectrophoretic force in this case is nN.

Out of those figures, for example, as can be seen from FIG. 12B, the strongest electrical field is generated in the vicinity of the edge of each guide electrode, and the weakest electrical field is generated between the guide electrodes (83 and 84). Further, a weak electrical field also exists in the vicinity of 0 μm and 100 μm in the y direction. With reference to FIGS. 14A and 14B, it is found that intensity gradients of the dielectrophoretic force are generated within a range of about 15 μm with respect to the center between the guide electrodes (83 and 84) and within a range of about 30 μm in the z direction.

As a result, by the guide electrical field formed, a steeper intensity gradient in the y direction than the intensity gradient in the z direction can give a dielectrophoretic force that is attracted to a direction toward the center between the guide electrodes 83 and 84.

A movement performance in the y direction of the particles in the direction change portion 82b of the guide electrode structure 82 is mainly determined by the bend angle α of the direction change portion 82b the speed of the liquid in the mainstream direction. The movement performance is defined in accordance with the degree of the dielectrophoretic force that operates in the y direction on a region boundary (curved surface represented by $F_{DEPz}$=0) where the dielectrophoretic force in the downward z direction operates.

Figure 15:
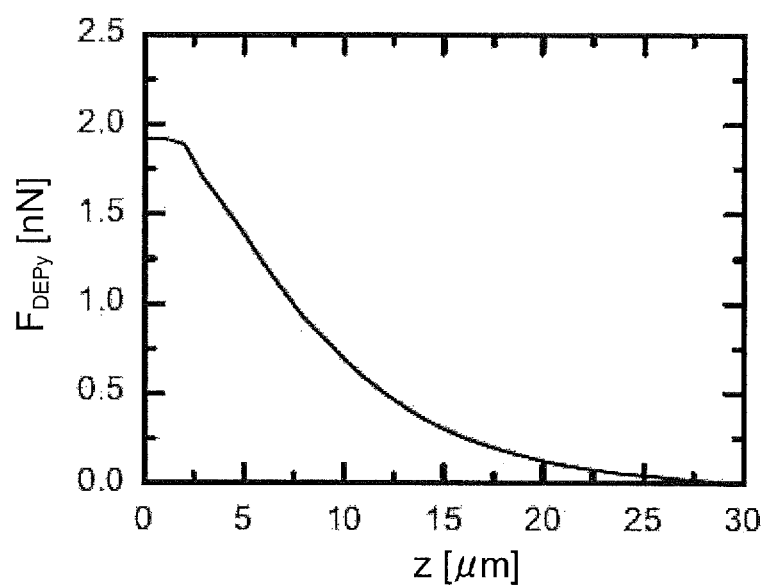
FIG. 15 is a diagram showing a degree of the dielectrophoretic force that operates in the y direction on a boundary where positive and negative dielectrophoretic forces in the z direction are switched at a position of a height z.

FIG. 15 is a diagram showing the degree of the dielectrophoretic force $F_{DEPy}$ (including rightward and leftward dielectrophoretic forces that are directed toward the center between the guide electrodes 83 and 84 in this case) that operates in the y direction on a boundary where positive and negative dielectrophoretic forces in the z direction are switched at a position of the height z. From FIG. 15, it is found that $F_{DEPy}$ is significantly changed in the z direction and is stronger as the height position is lower. That is, depending on an equilibrium position in the height direction of the movement of the particles, performance to be obtained (that is, $F_{DEPy}$ toward inside) is significantly changed. The equilibrium position in the height direction is significantly affected by the size of the particle or a force that acts on the particle from the liquid in proximity to a wall surface of the flow channel.

In this embodiment, it is possible to align the particles in the middle flow channel area and cause the particles to flow out into the input hole. Thus, it is possible to flow the particles with the particles aligned without positional variations also in the height direction of the flow channel. As a result, it is possible to stabilize the dielectrophoretic force $F_{DEPy}$ that acts on the particles.

Figure 16:
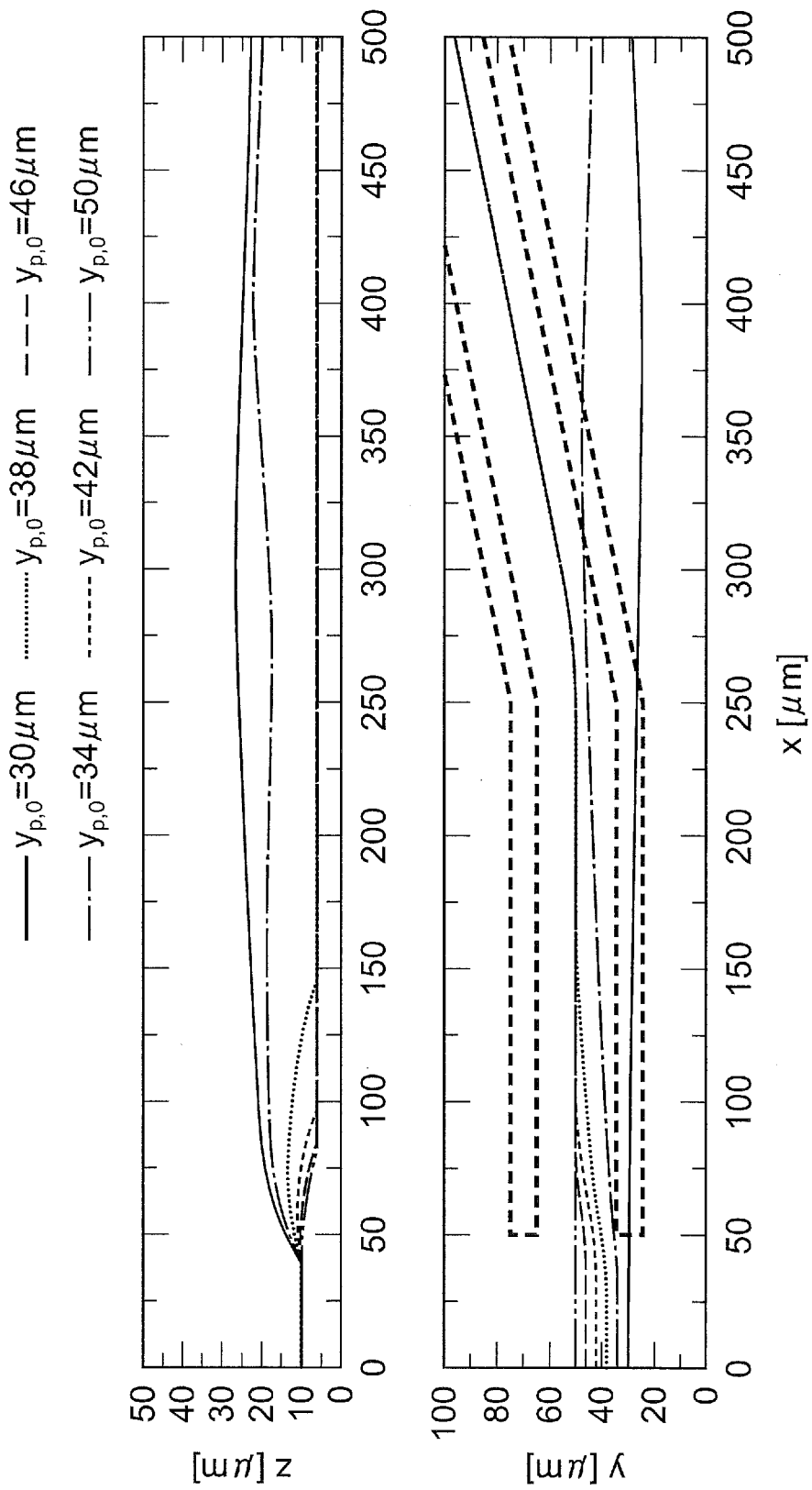
FIG. 16 is a diagram showing a simulation result of tracks of particles in the case where the particles flow into a flow channel area of a guide electrode structure from different positions in the y direction.

FIG. 16 is a diagram showing a simulation result of tracks of particles in the case where the particles flow into an area where the guide electrode structure 82 is disposed from different positions in the y direction. The upper diagram of FIG. 16 is viewed in the y direction, and the lower diagram thereof is viewed in the z direction.

As shown in the lower graph of FIG. 16, out of the particles that flow into the area in the guide electrode 83, particles other than particles ($y_{p,0}$=34 μm) having a track indicated by a dotted and dashed line move through a path along the guide electrodes 83 and 84. Particles that pass through an area closer to the center between the guide electrodes 83 and 84 in the y direction are less likely to be affected by the dielectrophoretic force in the upward z direction, and stably move through a path along the guide electrode structure 82 by $F_{DEPy}$ toward inside and the dielectrophoretic force in the downward z direction. Particles that pass through an area which is more distant from the center between the guide electrodes 83 and 84 in the y direction are more likely to be affected by the dielectrophoretic force in the upward z direction, but moves through the path along the guide electrode structure 82 by a force attracted to the center by $F_{DEPy}$ toward inside.

The particles having the track indicated by the dotted and dashed line are brought into a state where the height in the z direction is relatively high in the vicinity of x=50 μm, and $F_{DEPy}$ becomes small (see, FIG. 15), and therefore the particles go straight in the x direction as they are. Further, the particles that flow into the area above the guide electrode 84 (particles having a track indicated by the solid line ($y_{p,0}$=30 μm)) also show the same result. By using the flow channel device (particle outflow unit) according to the present technology, it is possible to prevent generation of the particles that flow along such a track and achieve sorting of the particles with high accuracy.

As described above, by the sorting flow channel unit 55 according to this embodiment, because the area of the common electrode 81 and the area of the guide electrode 83 (and 84) are different from each other, the sorting electrode unit 8 is capable of forming the guide electrical field having the non-uniform electric flux density in the flow channel 2. In addition, because the guide electrical field is formed so that the target particle C1 is guided to the branch channel 2a predetermined, the sorting flow channel unit 55 is capable of sorting the particles appropriately.

Further, the shapes of the guide electrodes 83 and 84 are elongated shapes. Therefore, as the width of the common electrode 81 is longer than those of the guide electrodes 83 and 84, the degree of freedom of positioning of the guide electrodes 83 and 84 with respect to positioning of the common electrode 81 is increased in the manufacture of the sorting flow channel unit 55. In other words, a precise alignment of the guide electrodes 83 and 84 with respect to the common electrode 81 is unnecessary. Furthermore, as a result, the productivity of the sorting flow channel unit 55 is improved, and thus it is possible to save the cost.

In this embodiment, the two elongated guide electrodes 83 and 84 are provided, with the result that the guide electrical field is easily formed, and the particles are easily guided to the branch channel 2a. Thus, it is possible to increase the sorting accuracy.

It should be noted that the structure of the sorting flow channel unit 55 is not limited, and various structures may be used therefor. By using the flow channel device according to the present technology, it is possible to cause the particles to flow in the flow channel with the particles aligned, so the particles can be sorted with high accuracy.

(Another Structural Example of Sorting Flow Channel Unit)

Figure 17:
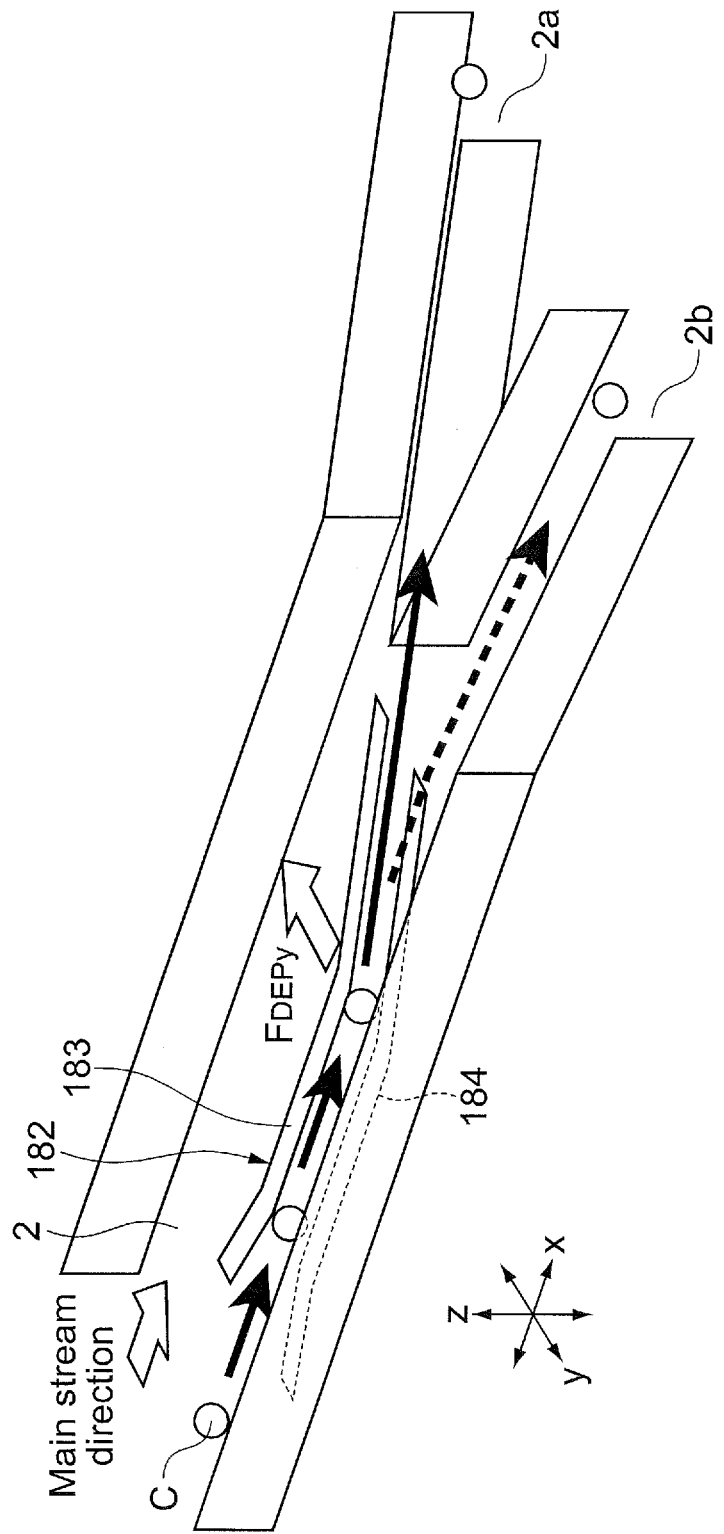
FIG. 17 is a schematic perspective view showing another structural example of a sorting flow channel unit.
Figure 18:
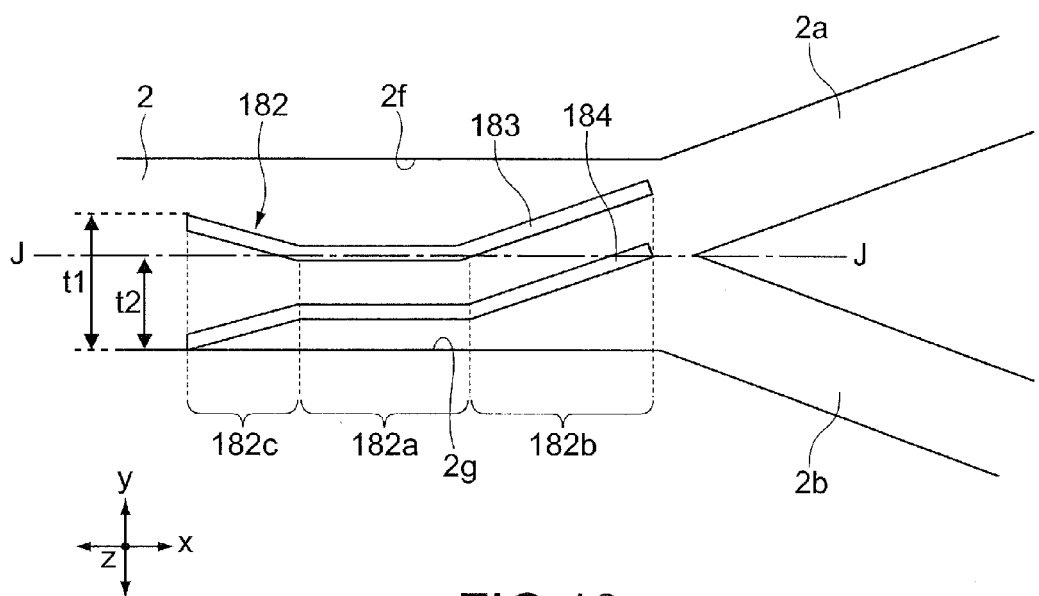
FIG. 18 is a schematic plan view showing the sorting flow channel unit shown in FIG. 17.

FIG. 17 is a schematic perspective view showing another structural example of the sorting flow channel unit 55, and FIG. 18 is a schematic plan view thereof. In the following description, the description of the same parts, functions, and the like as in the structural example described above will be simplified or omitted, and different points will be mainly described.

A guide electrode structure 182 according to this structural example has an entrance portion 182c provided at an end portion on the upstream side thereof. Here, a linear portion 182a and a direction change portion 182b are set as a main portion. In the entrance portion 182c, a distance between the guide electrodes 183 and 184 is formed to be longer than a distance therebetween in the main portion. In this embodiment, the distance between the guide electrodes 183 and 184 in the entrance portion 182c is formed so as to be increased toward the upstream side. More specifically, both of the two guide electrodes 183 and 184 are bent so that directions thereof are changed from the mainstream direction toward the upstream side.

A common electrode (not shown) has the same shape and the like as the common electrode 81 according to the structural example described above.

Because of the shape of the entrance portion 182c of the guide electrode structure 182 as described above, the particles C are likely to be attracted into an area between the guide electrodes 183 and 184 in the main portion of the guide electrode structure 182. Therefore, it is possible to provide a wide acceptable range for an outflow position of the particles by the flow channel device according to the present technology, that is, in relation to which part of the input hole 3c the middle flow channel area in which the particles flow is fit to. Further, the degree of freedom for disposition of the input hole 3c in the y direction is also increased.

Figure 19:
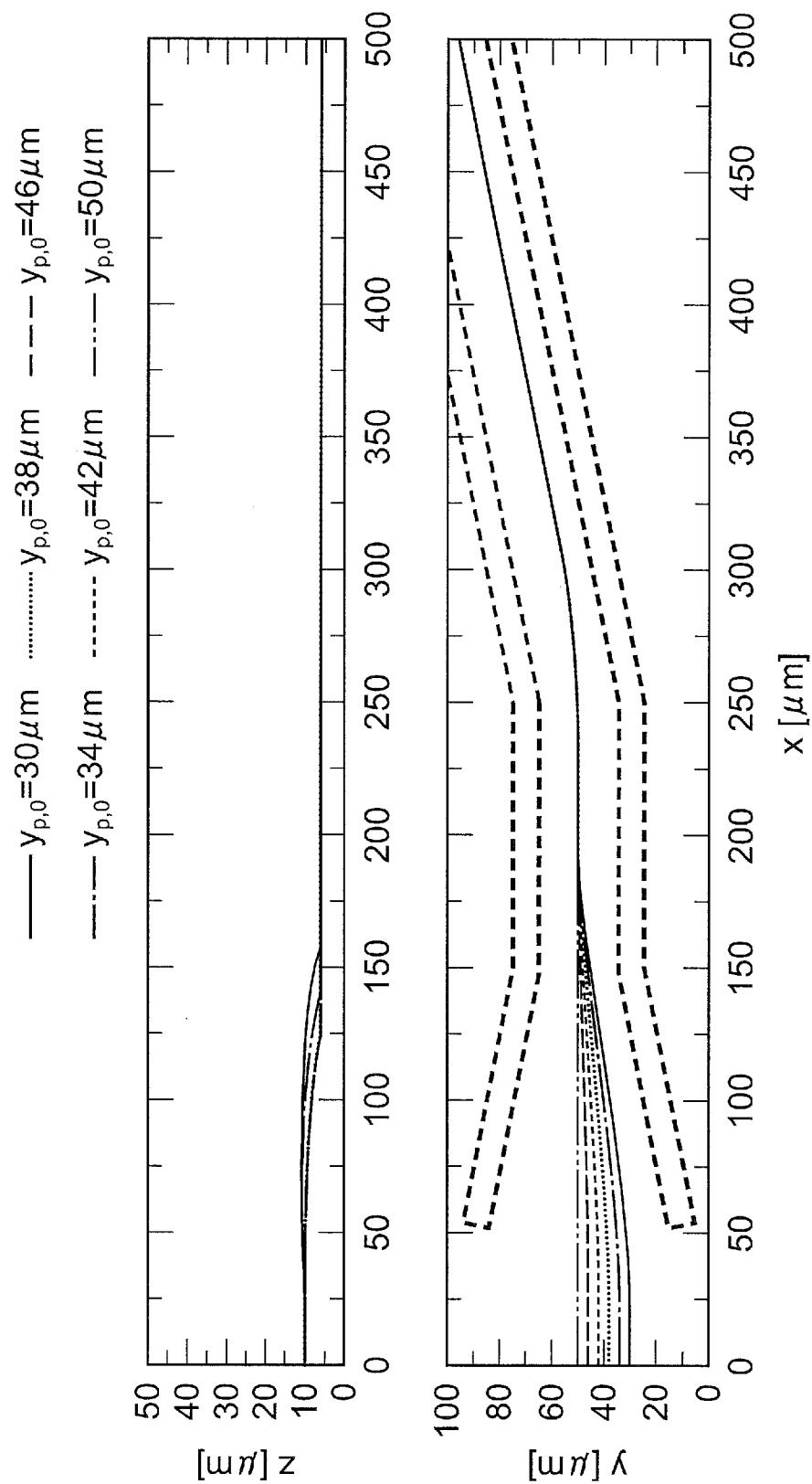
FIG. 19 is a diagram showing a simulation result of tracks of the particles with the sorting flow channel unit.

FIG. 19 is a diagram showing a simulation result of tracks of the particles with the sorting flow channel unit shown in FIGS. 17 and 18. The intent of this simulation is the same as that described with reference to FIG. 16. In the simulation shown in FIG. 19, the particles having the same variations similar to the case of FIG. 16 in the y direction are entirely attracted to the area between the guide electrodes 183 and 184.

Figure 20A:
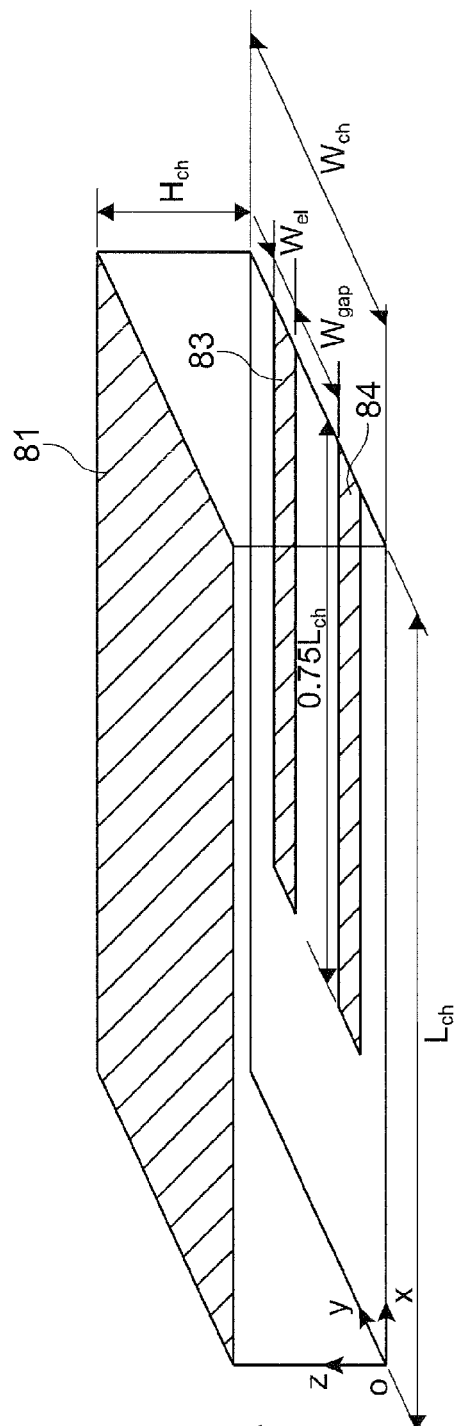
FIGS. 20A and 20B are diagrams showing design examples of approach sections of the guide electrode structures according to the two structural examples, respectively.
Figure 20B:
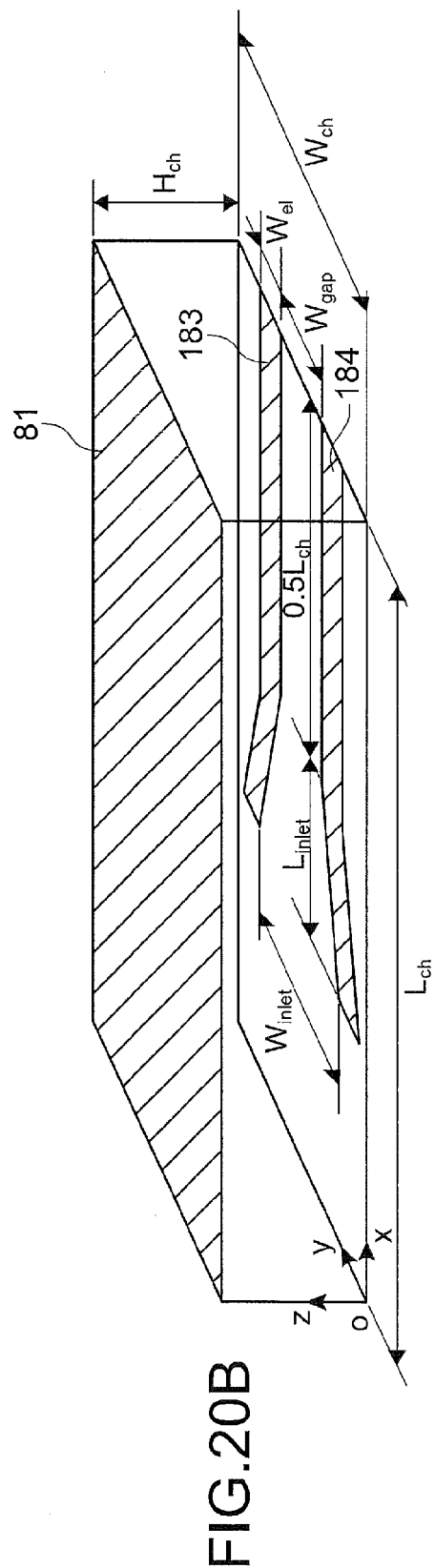

It should be noted that FIGS. 20A and 20B are diagrams showing design examples of approach sections of the guide electrode structures 82 and 182 according to the two structural examples described above, respectively. The values of those figures may be values shown in the table on the lower part of FIG. 11.

To efficiently guide the particles by the guide electrical field, the bend angle, the size, the shape of the entrance portion, and the like can be designed in consideration of a particle size, a height, a width of the flow channel in accordance with a liquid material, or the velocity of the particle, for example.

As an example, as shown in FIG. 18, a width t1 of the end portion of the entrance portion 182c on the upstream side is designed as follows. The width t1 is set to be larger than a distance from an inner side surface 2g provided on the branch channel 2b side in the y direction, out of an inner side surface 2f and the inner side surface 2g of the flow channel 2, which are opposed to each other, to the branch position of the branch channel 2a and the branch channel 2b in the y direction (i.e., distance to the branch reference line J).

Alternatively, as shown in FIG. 18, the guide electrode structure 182 is designed so that at least a part of the entrance portion (182c) of the guide electrode 183 on the branch channel 2a side in the y direction, of the pair of the guide electrodes 183 and 184, is disposed on the branch channel 2a side in the y direction from the branch position of the branch channels 2a and 2b.

Alternatively, in consideration of the variation of positions where the particles exist in the y direction, the distance between the guide electrodes 183 and 184 of the entrance portion 182c may be designed. For example, when the variation in the y direction is represented in a normal distribution, in the case of a standard deviation σ, the width t1 of the end portion of the entrance portion 182c on the upstream side may set to have a width (that exceeds 1σ) larger than a width of σ.

In this embodiment, it is possible to cause the particles flow with the particles aligned by the particle outflow unit, with the result that a burden on the design for the guide electrode structure as described above can be reduced. That is, the variation of the particles in the y direction is small (i.e., the standard deviation σ takes a small value), so the particles can be efficiently guided without strictly setting the distance between the guide electrodes 183 and 184.

Figure 21:
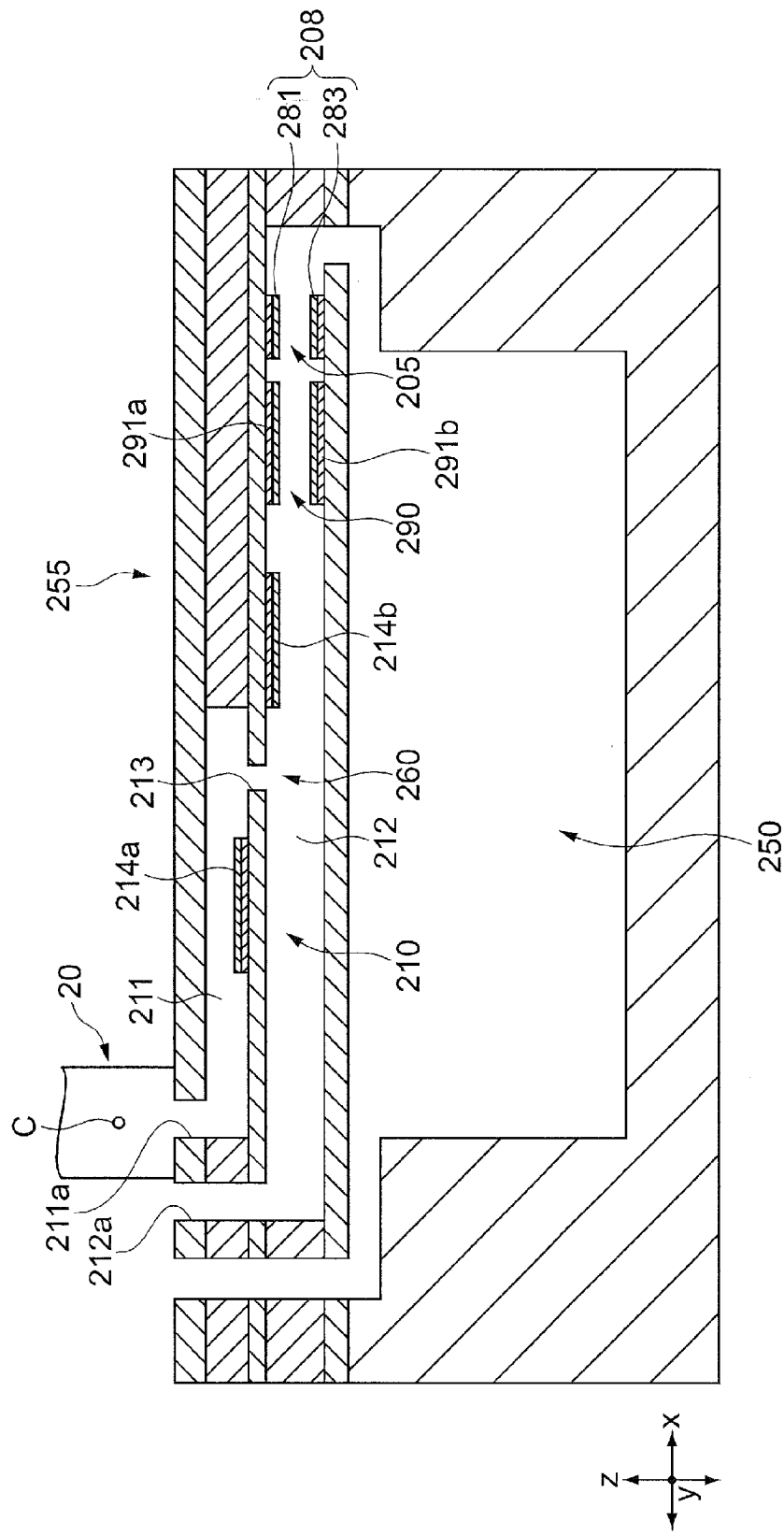
FIG. 21 is a diagram showing another structural example of the sorting flow channel unit for sorting the particles caused to flow out from the flow channel device.
Figure 22:
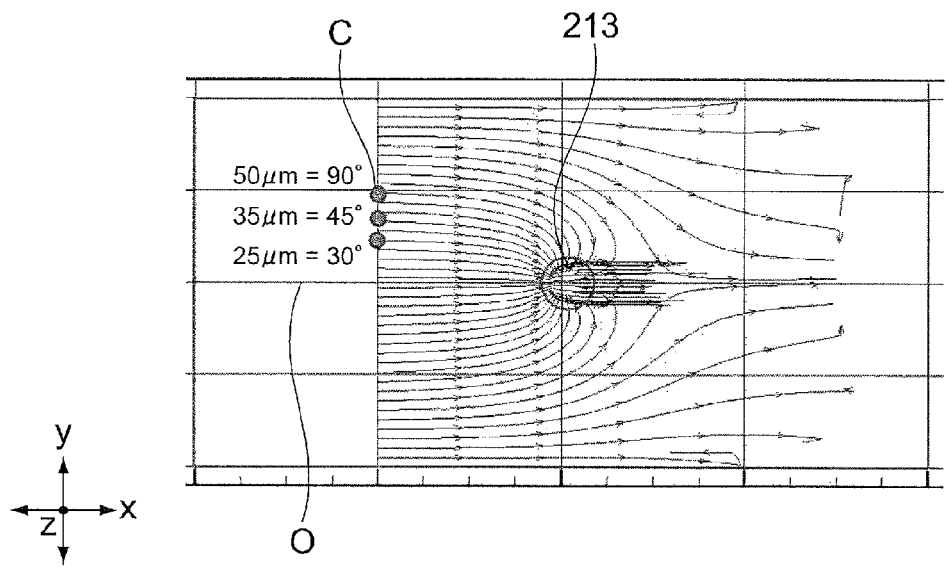
FIG. 22 is a diagram showing a simulation result of tracks of the particles that are caused to flow into a narrow channel from different positions in a flow channel width direction of a first flow channel.
Figure 23:
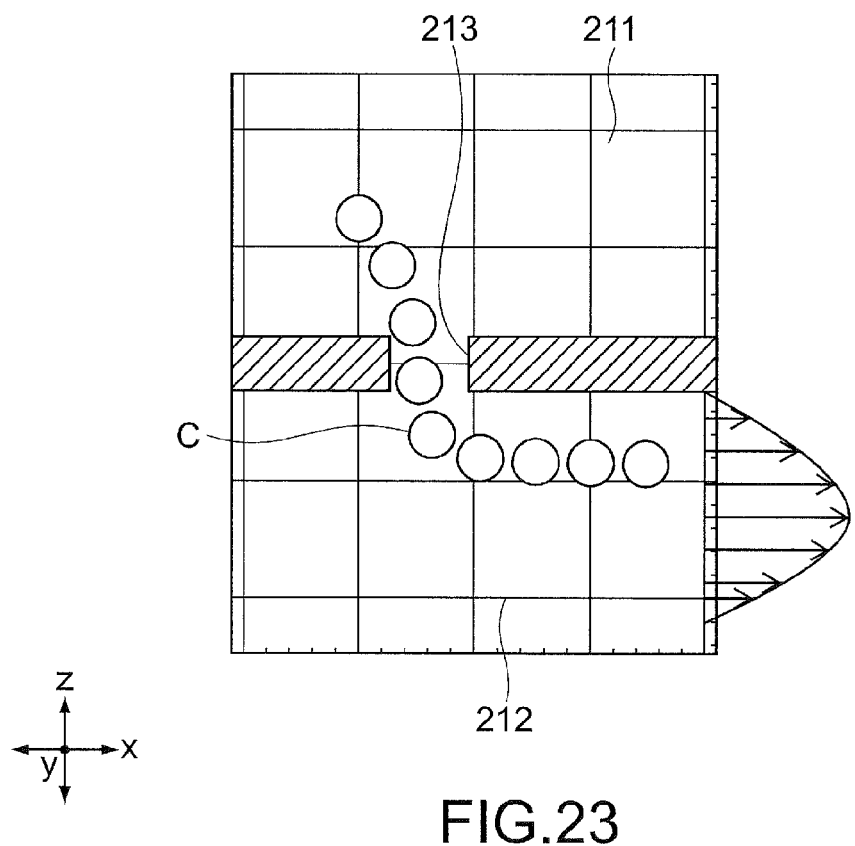
FIG. 23 is a schematic diagram of a track of a cell and a velocity distribution in a height direction of a second flow channel in the sorting flow channel unit.

FIGS. 21 to 23 are diagrams for explaining effectiveness of the flow channel device 20 (particle outflow unit 20) according to the present technology. FIG. 21 is a diagram showing another structural example of a sorting flow channel unit 255 for sorting the particles C caused to flow out by the flow channel device 20. The sorting flow channel unit 255 is provided with a flow channel 210 having two stages in a thickness direction (z direction) of the sorting flow channel unit 255. In FIG. 21, a first flow channel 211 provided on an upper stage has a first inlet 211a. On the first inlet 211a, the flow channel device 20 according to the present technology is disposed, and the middle flow containing the particles C and the peripheral flow that surrounds the middle flow are caused to flow out to the first inlet 211a. The particles C are caused to flow in a predetermined flow channel area (typically, middle flow channel area) of the first flow channel 211 with the particles aligned.

A second flow channel 212 provided on the lower stage has a second inlet 212a. The transfer fluid that does not contain the particles C is caused to flow to the second flow channel 212 via the second inlet 212a with a pump (not shown) or the like. As shown in FIG. 21, the first flow channel 211 and the second flow channel 212 are communicated with each other through a narrow channel 213 formed on a predetermined position. The narrow channel 213 has such a size as to allow particles to pass therethrough one by one. The particles C caused to flow in the first flow channel 211 in the aligned state are caused to flow into the second flow channel 212 via the narrow channel 213.

In the sorting flow channel unit 255 shown in FIG. 21, an area including the narrow channel 213 serves as a measurement unit 260. The measurement unit 260 includes measurement electrodes 214a and 214b with the narrow channel 213 sandwiched therebetween. The measurement electrodes 214a and 214b corresponds to the measurement electrodes 4a and 4b shown in FIG. 2 and are provided on the lower side of the first flow channel 211 and on the upper side of the second flow channel 212, respectively. To the measurement electrodes 214a and 214b, an AC voltage is applied, and an electrical characteristic at a time when the particles pass through the narrow channel 213 is measured.

On the downstream side of the second flow channel 212, a guard unit 290 and a sorting unit 205 are provided in the stated order. The guard unit 290 includes guard electrodes 291a and 291b disposed so as to be opposed on the upper side and the lower side of the second flow channel 212, respectively. The guard electrodes 291a and 291b form an electrode pair and are connected to ground. The guard unit 290 is disposed between the measurement unit 260 and the sorting unit 205 and exerts an electrical guard function therebetween. For example, by the guard unit 290, it is possible to suppress a noise due to a voltage signal applied to the sorting unit 205 from being mixed in the measurement unit 260.

The sorting unit 205 includes a sorting electrode unit 208 that forms a guide electrical field. As shown in FIG. 21, on the upper side of the second flow channel 212, a common electrode 281 is disposed, and a guide electrode 283 is disposed on the lower side of the second flow channel 212 so as to be opposed to the common electrode 281. The sorting electrode unit 208 forms the guide electrical field as necessary, and the dielectrophoretic force is given to the target particle. As a result, the target particle and the other particles are sorted, and the particles C are caused to flow to a predetermined particle obtaining unit 250.

FIG. 22 is a diagram showing a simulation result of tracks of the particles that are caused to flow in the narrow channel 213 from different positions in a flow channel width direction of the first flow channel 211. For example, in the flow channel width direction (y direction), the particle C that advances along a position significantly distanced from a reference line O that passes the center of the narrow channel 213 does not enter the narrow channel 213 but passes by the narrow channel 213. As a result, it may be impossible to sort the particles C. Further, for even the particles C that enter the narrow channel 213, if positions thereof vary in the flow channel width direction, positions of the particles C at a time when the particles C pass through the narrow channel 213 vary.

In the simulation shown in FIG. 22, the particle that advances along the reference line O directly flows in and passes through the narrow channel 213 and then flows into the second flow channel 212. Therefore, in this case, along the reference line O (at an angle of O degree with respect to the reference line O), the particle C flows in the narrow channel 213. The particle that advances along a position distanced from the reference line O by 25 μm in the flow channel width direction flows in the narrow channel 213 at an angle of approximately 30 degrees with respect to the reference line O. The particle C that advances along a position distanced therefrom by 35 μm flows in the narrow channel 213 at an angle of approximately 45 degrees. The particle C that advances along a position distanced therefrom by 50 μm flows in the narrow channel 213 at an angle of approximately 90 degrees. In this way, when the angles at which the particles flow in the narrow channel 213 are different, the positions along which the particles C advance in the narrow channel 213 are also different. Thus, due to the variation of the position in the flow channel in the flow channel width direction, the variation in passing positions in the narrow channel is caused. The occurrence of the variation in passing positions in the narrow channel results in a reduction of accuracy of the measurement by the measurement unit 260 and the analysis for a signal measured. As a result, accuracy of determining the target particles is also degraded.

In addition, as described above, in association with the variation in the passing positions in the narrow channel, if the positions of the particles vary in the flow channel width direction and the height direction in the second flow channel 212, it becomes difficult to appropriately generate the dielectrophoretic force by the guide electrical field.

FIG. 23 is a schematic diagram of a track of a cell and a velocity distribution in the height direction of the second flow channel 212 in the sorting flow channel unit 255. As shown in FIG. 23, in the height direction of the second flow channel 212, the flowing velocity of the particle C differs. The velocity is increased in the middle portion of the second flow channel 212 in the height direction, and is reduced toward the upper side and the lower side. Due to the variation in the passing position in the narrow channel of the particles, the height position of the particles C that flow in the second flow channel 212 varies, with the result that the flowing velocity of the particles varies. If the velocity of the particles C that advance in the second flow channel 212 varies, it becomes difficult to adjust a sorting timing (timing at which the guide electrical field is generated) by the sorting unit 205, which degrades the sorting accuracy.

As described above, if the particles C caused to flow out in the first flow channel 211 vary in the flow channel width direction, various factors that degrade the sorting accuracy are caused. In view of this, it is very effective that the flow channel device 20 according to the present technology is used to cause the particles C to flow out in the first flow channel 211 with the particles C aligned. As a result of experimental confirmation of the simulation described above, by using the flow channel device 20, the positional variation in the first flow channel 211 in the flow channel width direction is reduced. Further, the particles pass through the narrow channel 213 at a constant height, with the result that the particle velocity in the second flow channel 212 is stabilized. As a result, it is possible to sort the particles with high accuracy.

Other Embodiments

The present technology is not limited to the above embodiments, and various other embodiments can be implemented as follows.

Figure 24:
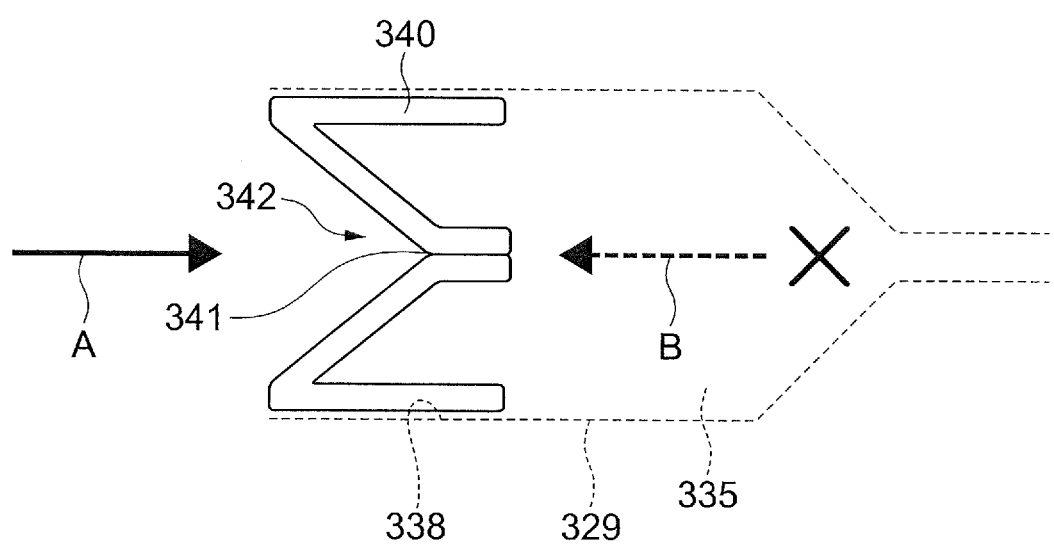
FIG. 24 is a schematic diagram showing another structural example of a sealing member for sealing a particle supply port of a middle outflow unit.

For example, FIG. 24 is a schematic diagram showing another structural example of a sealing member 340 for sealing a particle supply port 338 of a middle outflow unit 329. For example, in a sample injection process as shown in FIG. 24, a valve or the like made of elastomer, which is opened and closed by an insertion operation (arrow A) of a pipette, may be used as the sealing member 340. When the pipette is inserted in an insertion hole 341, by the insertion pressure, an opening and closing unit 342 is opened, and the pipette is inserted therein. In this state, a sample is supplied to a space unit 335 in the middle outflow unit 329 via the pipette. After the sample is supplied, the pipette is removed, and thus the opening and closing unit 342 is closed, thereby sealing the particle supply port 338. Even if a pressure is applied from the inside of the sealing member 340 (arrow B), the opening and closing unit 342 is not opened and closed, and the particle supply port 38 is appropriately sealed. Such a device as to have the structure like a check valve may be used. Further, a member having a function of adjusting the pressure in the space unit 335 may be used as the sealing member 340.

In addition, the particle supply port 338 is not sealed but opened to the atmosphere, and the middle flow and the peripheral flow may be flow out. For example, by appropriate container configuration design and pressure loss design, it is possible to achieve such a structure that the sample is not leaked to the outside (atmosphere side) of the device. For example, a negative pressure is given to the merged part and the downstream side of the main flow channel to perform operation, such a structure can be achieved. As a result, it is possible to simplify the structure of the holding unit.

By appropriately designing the structure of the sealing member as described above or designing the container configuration or the like with the supply port opened, for example, when the middle flow and the peripheral flow can be caused to flow out in the micro flow channel without splitting the transfer fluid from the transfer fluid inflow port, the same effect as described above can be exerted. The flow channel device having such a structure can be considered as a device conceptually having the same technical idea as the flow channel device according to the present technology. That is, it can be considered that the above technology is contained as the technology for maintaining the flow rate ratio between the middle flow and the peripheral flow to be constant in the small flow rate area with approximately 1 µL per minute. Further, the flow channel devices as described above (for example, flow channel device that splits the transfer fluid to make the flow rate ratio constant, flow channel device that makes the flow rate ratio constant with a different structure, or the like) can be used as interchangeable devices as necessary.

Figure 25A:
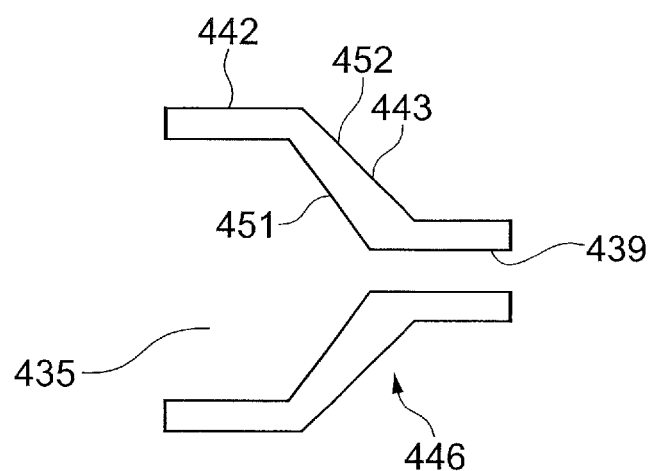
FIGS. 25A to 25C are schematic diagrams each showing another structural example of the middle outflow unit to a particle outflow port.
Figure 25B:
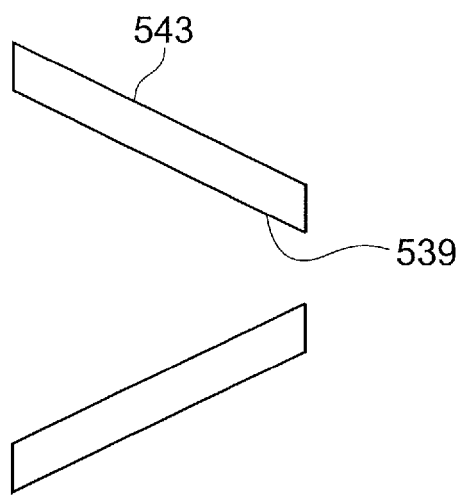
Figure 25C:
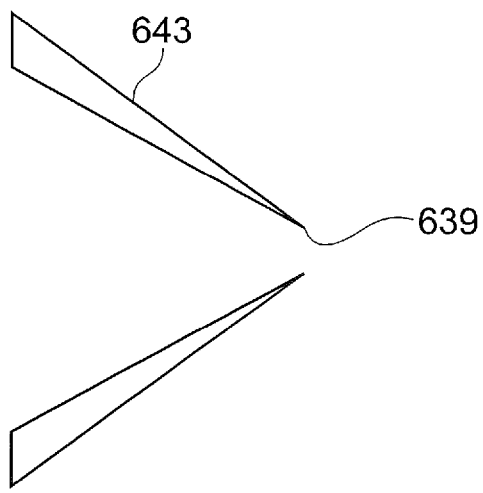

FIGS. 25A to 25C are schematic diagrams showing other structural examples of a middle outflow channel up to particle outflow ports (439, 539, and 639), respectively. As shown in FIG. 25A, in a tapered unit 443 the diameter of which is gradually reduced from a side wall unit 442 to the particle outflow port 439, an inner surface 451 and an outer surface 452 may have different tilt angles. The tilt angles of the inner surface 451 and the outer surface 452 may be individually designed in accordance with the flow of the transfer fluid in a space unit 435 and the flow of the transfer fluid in a peripheral outflow channel 446.

In FIG. 25B, a tapered unit 543 is formed as a middle outflow channel as it is. That is, at a lowermost end part of the tapered unit 543, the particle outflow port 539 is formed. With this structure, it is possible to simplify the structure of the middle outflow unit. In this case, as shown in FIG. 25C, a tapered unit 634 may be designed to have a thickness which is gradually reduced toward the particle outflow port 639.

As shown in FIGS. 3 and 4, as described above, the peripheral outflow channel 46 is formed concentrically with the particle outflow port 39 as the center. With this structure, the particles C can be caused to stably flow out with the particles C aligned in the middle flow channel area 28. However, for example, the peripheral outflow channel 46 may not be formed concentrically. That is, the particle outflow port 39 may be disposed at an eccentric position with respect to the annular peripheral outflow channel 46. With this structure, it is possible to appropriately set the position to which the particles C are desired to be caused to flow. It should be noted that in the above description, the predetermined area to which the particles C are desired to be caused to flow is set as the middle flow channel area 28. However, the predetermined area is not limited to the middle of the flow channel. The position of the particle outflow port 39 may be appropriately fitted to the position to which the particles C are desired to be caused to flow.

The direction in which the particles in the flow channel device according to the present technology are caused to flow out is not limited to the direction of gravity. For example, the flow channel device may be disposed along a horizontal direction, and the particles may be caused to flow in the horizontal direction. In addition to this, the angle at which the particles are caused to flow out may be set arbitrarily. Further, the extended direction of the flow channel as an outflow destination is not also limited. There is no limitation on the use of the flow channel device according to the present technology in order to cause the particles to flow to the main flow channel that is extended in the horizontal direction as described above. Further, the direction of the route to the outflow destination of the sorting apparatus, the flow channel device, or the like and the structures thereof are not also limited (for example, connection unit 52 shown in FIG. 6).

In the above description, to cause the particles to flow out to the particle sorting apparatus, the flow channel device according to the present technology is used. However, the structure is not limited to this. The flow channel device according to the present technology may be used for an apparatus for analyzing the particles or another apparatus. That is, the use purpose of causing the particles to flow out, the kind of the particles, and the like are not limited.

As the guide electrode structure according to the above structural example, two guide electrodes are given as an example. However, three or more guide electrodes may be provided.

In addition, the drive voltage which is applied to the sorting electrode unit is the AC voltage but may be a DC voltage.

The flow channel, the branch channel, and the like described above each have the linear shape but may have a curved shape. The cross section of the flow channel has the rectangular shape but may have a circular shape, an oval shape, a polygonal shape other than the rectangle, or a shape obtained by combining those shapes.

The common electrode has the rectangular shape but may have a circular shape, an ellipse, an oval shape, a polygonal shape, or any other shape. Further, the shape of the common electrode can differ depending on the shape of the flow channel 2.

The measurement unit measures impedance depending on the particles but may measure a fluorescent intensity or a scattered light intensity depending on the particles. The analysis unit generates a sorting signal on the basis of the values measured.

At least two of the features of the embodiments described above can be combined.

It should be noted that the present technology can take the following configurations.

(1) A flow channel device, including:
an inflow unit into which a transfer fluid that transfers particles is caused to flow;
a first outflow unit including an inflow port into which a part of the transfer fluid caused to flow from the inflow unit is caused to flow, a holding unit that is connected to the inflow port and holds particles, and a particle outflow port from which the particles held in the holding unit are caused to flow out to a predetermined flow channel area by the transfer fluid caused to flow from the inflow port; and
a second outflow unit including a peripheral outflow channel through which another part of the transfer fluid caused to flow from the inflow unit is caused to flow out to a peripheral flow channel area that surrounds the predetermined flow channel area, the peripheral outflow channel surrounding at least the particle outflow port.

(2) The flow channel device according to Item (1), in which
the first and second outflow units respectively cause the particles and the transfer fluid to flow out as a laminar flow having a Reynolds number of 1 or less.

(3) The flow channel device according to Item (1) or (2), in which
the first and second outflow units respectively cause the particles and the transfer fluid to flow out in such a manner that a ratio between a flow rate in the predetermined flow channel area and a flow rate in the peripheral flow channel area falls within a range of 1:2 to 1:100.

(4) The flow channel device according to any one of Items (1) to (3), in which
the peripheral outflow channel is disposed concentrically with the particle outflow port as a center.

(5) The flow channel device according to any one of Items (1) to (4), in which
the holding unit includes
a supply port for supplying the particles, the supply port having a diameter larger than that of the particle outflow port, and
a main body unit having a funnel-like shape, the main body unit including a tapered unit which connects the supply port and the particle outflow port with each other and a diameter of which is reduced from the supply port toward the particle outflow port.

(6) The flow channel device according to Item (5), in which
the supply port is sealed by a sealing member.

(7) The flow channel device according to Item (5), in which
the supply port is in a state of being released to an atmosphere.

(8) The flow channel device according to any one of Items (1) to (7), in which
the particle outflow port has a diameter that is smaller than ten times a diameter of the particle.

It should be understood by those skilled in the art that various modifications, combinations, sub-combinations and alterations may occur depending on design requirements and other factors insofar as they are within the scope of the appended claims or the equivalents thereof.

What is claimed is:

1. A flow channel device, comprising:
an inflow unit into which a transfer fluid that transfers particles is caused to flow;
a first outflow unit including an inflow port into which a part of the transfer fluid caused to flow from the inflow unit is caused to flow, a holding unit that is connected to the inflow port and holds particles, and a particle outflow port from which the particles held in the holding unit are caused to flow out to a predetermined flow channel area by the transfer fluid caused to flow from the inflow port; and
a second outflow unit including a peripheral outflow channel through which another part of the transfer fluid caused to flow from the inflow unit is caused to flow out to a peripheral flow channel area that surrounds the predetermined flow channel area,
wherein the peripheral outflow channel is surrounding at least the particle outflow port,
wherein the entire peripheral outflow channel has a circular cross section along a plane in a direction perpendicular to a direction of flow of the particles in the predetermined flow channel area.

2. The flow channel device according to claim 1, wherein the first and second outflow units respectively cause the particles and the transfer fluid to flow out as a laminar flow having a Reynolds number of 1 or less.

3. The flow channel device according to claim 1, wherein the first and second outflow units respectively cause the particles and the transfer fluid to flow out in such a manner that a ratio between a flow rate in the predetermined flow channel area and a flow rate in the peripheral flow channel area falls within a range of 1:2 to 1:100.

4. The flow channel device according to claim 1, wherein the peripheral outflow channel is disposed concentrically with the particle outflow port as a center.

5. The flow channel device according to claim 1, wherein the holding unit includes
a supply port for supplying the particles, wherein the supply port have a diameter larger than that of the particle outflow port, and
a main body unit having a funnel shape, wherein the main body unit includes a tapered unit which connects the supply port and the particle outflow port with each other and a diameter of which is reduced from the supply port toward the particle outflow port.

6. The flow channel device according to claim 5, wherein the supply port is sealed by a sealing member.

7. The flow channel device according to claim 5, wherein the supply port is in a state of being released to an atmosphere.

8. The flow channel device according to claim 1, wherein the particle outflow port has a diameter that is smaller than ten times a diameter of the particle.

9. A particle outflow method, comprising:
- causing a transfer fluid that transfers particles to flow into an inflow unit;
- causing a part of the transfer fluid caused to flow from the inflow unit to flow into a holding unit that holds particles, thereby causing the particles held in the holding unit to flow out to a predetermined flow channel area through a particle outflow port; and
- causing another part of the transfer fluid caused to flow from the inflow unit to flow out to a peripheral flow channel area that surrounds the predetermined flow channel area via a peripheral outflow channel that surrounds the particle outflow port,
    - wherein the entire peripheral outflow channel has a circular cross section along a plane in a direction perpendicular to a direction of flow of the particles in the predetermined flow channel area.

* * * * *